US 6,489,311 B1

(12) United States Patent
Kennedy

(10) Patent No.: US 6,489,311 B1
(45) Date of Patent: Dec. 3, 2002

(54) METHOD FOR THE PREVENTION OF APOPTOSIS

(75) Inventor: Thomas P. Kennedy, Charlotte, NC (US)

(73) Assignee: Charlotte-Mecklenburg Hospital Authoirty, Charlotte, NC (US)

( * ) Notice: Subject to any disclaimer, the term of this patent is extended or adjusted under 35 U.S.C. 154(b) by 0 days.

(21) Appl. No.: 09/561,663

(22) Filed: May 2, 2000

(51) Int. Cl.[7] .......................... A01N 43/04; A61K 9/127
(52) U.S. Cl. .......................................... 514/56; 424/450
(58) Field of Search ............................. 514/56; 424/450

(56) References Cited

U.S. PATENT DOCUMENTS 4,239,754 A * 12/1980 Sache et al. ................. 424/183
5,668,118 A * 9/1997 Kennedy ...................... 514/56

OTHER PUBLICATIONS

Barzu et al. "O–Acylated heparin derivatives with low anticoagulant activity decrease proliferation and increase alpha–smooth muscle actin expression in cultured arterial smooth muscle cells" European Journal of Pharmacology 219 (1992) pp. 225–233.*
A. Saraste, et al., *Apoptosis In Human Myocardial Infarction*, Circulation, 95:320–323, 1997.
A. Ashkenazi, and V.M. Dixit, *Death Receptors: Signaling And Modulation*, Science, 281:1305–1308, 1998.
D.R. Green, and J.C. Reed, *Mitochrondria And Apoptosis*, Science, 81:1309–1312, 1998.
A. Haunstetter, and S. Izumo, *Basic Mechanisms And Implications For Cardiovascular Diseases*, Circ. Res., 82:1111–1129, 1998.
J. Narula, et al., *Apoptosis In Myocytes In End–Stage Heart Failure*, New England J. Med., 335:1182–1189, 1996.
T. Kubota, et al., *Dilated Cardiomyopathy In Transgenic Mice With Cardiac–Specific Overexpression Of Tumor Necrosis Factor–α* Circ. Res., 81:627–635, 1997.
B.S. Cain, et al., *Therapeutic Strategies To Reduce TNF–A Mediated Cardiac Contractile Depression Following Ischemia And Reperfusion*, J. Mol. Cell. Cardiol., 31:931–947.
D.R. Meldrum, et al., *Hemorrhage Activates Myocardial NFkB And Increases TNF–α In The Heart*, J. Mol. Cell. Cardiol., 29:2849–2854, 1997.

(List continued on next page.)

Primary Examiner—Jezia Riley
(74) Attorney, Agent, or Firm—Alston & Bird LLP

(57) ABSTRACT

Heparin reduces ischemia-reperfusion injury to myocardium. This effect has been attributed complement inhibition, but heparin also has other activities that might diminish ischemia-reperfusion. To further probe these mechanisms, we compared heparin and an O-desulfated nonanticoagulant heparin with greatly reduced anti-complement activity. Given at the time of coronary artery reperfusion in a canine model of myocardial infarction, both heparin and O-desulfated heparin equally reduced neutrophil adherence to ischemic-reperfused coronary artery endothelium, influx of neutrophils into ischemic-reperfused myocardium, myocardial necrosis and release of creatine kinase into plasma. Heparin and O-desulfated heparin also prevented dysfunction of endothelial-dependent coronary relaxation following ischemic injury. In addition, heparin and O-desulfated heparin inhibited translocation of the transcription factor NF-κB from cytoplasm to the nucleus in human endothelial cells and decreased NF-κB DNA binding in human endothelium and ischemic-reperfused rat myocardium. Thus, heparin and nonanticoagulant heparin decrease ischemia-reperfusion injury by disrupting multiple levels of the inflammatory cascade, including the novel observation that heparins inhibit activation of the pro-inflammatory transcription factor NF-κB.

14 Claims, 13 Drawing Sheets

OTHER PUBLICATIONS

G. Olivetti, et al., *Acute Myocardial Infarction In Humans Is Associated With Activation Of Programmed Myocyte Cell Death In The Surviving Portion Of The Heart, J. Mol. Cell Cardiol.*, 28:2005–2016, 1994.

C. Chen, et al., *Myocardial Cell Death And Apoptosis In Hibernating Myocardium J.A.C.C.*, 30:1407–1412, 1997.

H. Akimoto, et al., *Heparin And Heparan Sulfate Block Angiotensin–II–Induced Hypertrophy in Cultured Neonatal Rat Cardiomyocytes. A Possible Role Of Intrinsic Heparin–Like Molicules In Regulation Of Cardiomyocyte Hypertrophy, Circ.*, 93:810–816, 1996.

C.A. Piot, et al., *Ischemic Preconditioning Decreases Apoptosis In Rat Hearts In Vivo, Circ.*, 96:1598–1604, 1997.

Y–T Xuan, et al., *Nuclear Factor–Kb Plays An Essential Role In The Late Phase Of Ischemic Preconditioning In Conscious Rabbits, Circ. Res*, 84:1095–1109, 1999.

J.C. Reed, *Cytochrome c:Can't Live With It, Can'T Live Without It, Cell*, 91:559–562, 1997.

H. Zou, et al., *Apaf–1, A Human Protein Homologous To C. Elegans CED–4, Participates In Cytochrome C–Dependents Activation Of Caspase–3, Cell*, 90:405–413, 1997.

M. Barinaga, *Stroke–Damaged Neurons May Commit Cellular Suicide, Science*, 281:1302–1303, 1998.

N.V. Rao, et al., *Sulfated Polysaccharides Prevent Human Leukocyte Elastase–Induced Lung Injury And Emphysema In Hamsters, Am. Rev. Respir. Dis*, 142:407–412, 1990.

J–M. Lee, et al., *The Changing Landscape Of Ischaemic Brain Injury Mechanisms, Nature*, 399 (Supplement):A7–A14, 1999.

J.M. Adams, et al., *The Bcl–2 Protein Family:Arbiters Of Cell Survival, Science*, 1326, 1998,.

L.C. Petersen, and R.P. Cox, *The Effect Of Complex Formation With Polyanions On The Redox Properties Of Cytochrome C, Biochem. J*, 2:687–693, 1980.

J. Bagelova, et al., *Studies On Cytochrome C–Heparin Interactions By Differential Scanning Calorimetry, Biochem. J.*, 297:99–101. 1994.

M. Antalik, et al., *Spectrophotometric Detection Of The Interaction Between Cytochrome C And Heparin, Biochem. Biophys, Acta*, 1100:155–159, 1992.

R. Von Harsdorf, et al., *Signaling Pathways In Reactive Oxygen Species–Induced Cardiomyocyte Apoptosis, Circ.*, 99:2934–2941, 1999.

S. Krajewski, et al., *Release Of Caspase–9 From Mitochondrial During Neuronal Apoptosis And Cerebral Ischemia, Proc. Natl. Acad. Sci. USA*, 96:5752–5757, 1999.

N. Maulik, et al., *Oxidative Stress Developed During The Reperfusion Of Ischemic Myocardium Induces Apoptosis, Free Rad. Biol. Med.*, 24:869–875, 1998.

C.Y. Wang, et al., *TNF– And Cancer THerapy Induced Apoptosis:Potential By Inhibition Of NF–kb, Science*, 274:784–789, 1996.

F.G. Wulczyn, et al., *The NF–kb And I kB Gene Families: Mediators Of Immune Response And Inflammation, J. Mol. Med.*, 74:749–769, 1996.

A.A. BEG, et al., *An Essential Role For NF13 kB In Preventing TNF–α–Induced Cell Death, Science*, 274:782–784, 1996.

T.C. Wright, et al., *Regulation Of Cellular Proliferation By Heparin And Heparin Sulfate. In Heparin. Chemical And Biological Properities. Clinical Applications.* D.A. Lane and U.Lindahl, editors, CRC Press, Inc., Boca Raton, FL 295–316.

G. Nunez and M. Clarke, *The Bcl–2 Family Of Proteins: Regulators Of Cell Death And Survival, Trends In Cell Biology*, vol. 4, Nov., 1994.

\* cited by examiner

METHOD FOR THE PREVENTION OF APOPTOSIS

FIELD OF THE INVENTION

This invention relates to a method for inhibiting apoptosis in ischemic-reperfused myocardium. More specifically this invention relates to a method for using heparin or noncoagulant heparin in the prevention of apoptosis.

BACKGROUND OF THE INVENTION

Cells die by one of either of two processes: necrosis or apoptosis. Whereas necrosis occurs through external injury producing cellular membrane destruction, swelling and lysis, apoptosis is endogenously mediated cellular suicide effected by activation of a series of aspartate-specific proteases called caspases and endonucleases, resulting in proteolytic destruction of cellular proteins and chromosomal elements. Apoptotic events include DNA fragmentation, chromatin condensation, membrane blebbing, cell shrinkage, and disassembly into membrane-enclosed vesicles (apoptotic bodies). In vivo, this process culminates with the engulfment of apoptotic bodies by other cells, preventing complications that would result from a release of intracellular contents. In myocardial infarction, both processes contribute to myocardial muscle injury and destruction. Overt necrosis predominates in the central zone of infarcted myocardium, and apoptosis occurs in the border zones of histologically infarcted myocardium. See, G. Olivetti, et al., "Acute myocardial infarction in humans is associated with activation of programmed myocyte cell death in the surviving portion of the heart," *J. Mol. Cell Cardiol*, 28:2005–2016, 1994; and A. Saraste, et al., "Apoptosis in human myocardial infarction," *Circulation*, 95:320–323, 1997. Also, apoptosis occurs in hypoperfused hibernating myocardium. See, C. Chen, et al., "Myocardial cell death and apoptosis in hibernating myocardium," *J.A.C.C*, 30:1407–1412, 1997. Apoptosis also contributes substantially to myocyte death in patients suffering heart failure from dilated cardiomyopathy. See, A. Haunstetter, et al., "Basic mechanisms and implications for cardiovascular diseases," *Circ. Res.*, 82:1111–1129, 1998.

Apoptosis is controlled at two distinct levels. First, cells have unique sensors, termed death receptors, on their membrane surface. Death receptors detect the presence of extracellular death signals and, in reponse, ignite the cell's intrinsic apoptosis machinery. See, A. Ashkenazi, et al., "Death receptors: signaling and modulation," *Science*, 281:1305–1308, 1998. One of the more important receptors is the member of the tumor necrosis receptor family TNFR1 (also called p55). When tumor necrosis factor (TNF) attaches to TNFR1, the receptor trimerizes, and binds a series of other proteins: TRADD ((TNFR-associated death domain); TRAF-2 (TNFR-associated factor-2; RIP (receptor-interacting protein): and FADD (Fas-associated death domain). FADD couples the TNFR1-TRADD complex to activate caspase-8, thereby initiating activation of the entire cascade of other caspases that effect apoptosis. TNF plays an important role in ischemia-reperfusion injury and in the contractile depression of myocardium following ischemia and reperfusion during myocardial infarction. See, B. S. Cain, et al., "Therapeutic strategies to reduce TNF-$\alpha$ mediated cardiac contractile depression following ischemia and reperfusion," *J. Mol. Cell. Cardiol.*, 31:931–947. TNF plays an important role in hemorhagic shock. See, D. R. Meldrum, et al., "Hemorrhage activates myocardial NF$\kappa$B and increases TNF-$\alpha$ in the heart," *J. Mol. Cell. Cardiol.*, 29:2849–2854, 1997. Apoptosis from TNF produced endogenously by overloaded myocardium also plays a significant role in mediating cardiac apoptosis leading to initiation and progression of congestive heart failure. See, for example, J. Narula, et al., Apoptosis in myocytes in end-stage heart failure," *New England J. Med,* 335:1182–1189, 1996; and T. Kubota, et al., et al., "Dilated cardiomyopathy in transgenic mice with cardiac-specific overexpression of tumor necrosis factor-$\alpha$," *Circ. Res.*, 81:627–635, 1997.

At a second site, activation of caspases and subsequent apoptosis are initiated by events that disturb mitochondria. Either disruption of electron transport and aerobic oxidative phosphorylation or opening of pores in the outer mitochondrial membrane by pro-apoptotic cytoplasmic proteins of the BAX or BH3 families will allow leakage out of the mitochrondria of the respiratory chain component cytochrome c. Upon entering the cytoplasm, cytochrome c binds to a cytosolic protein called apoptotic protease activating factor-1 (Apaf-1). In the presence of ATP, the complex of cytochrome c and Apaf-1 activate procaspase 9, which initiates subsequent activation of the remainder of the caspase cascade and initiation of cellular apoptosis. See, D. R. Green, et. al., "Mitochrondria and apoptosis," *Science,* 81:1309–1312, 1998.

The death domain and mitochrondrial pathways of caspase and apoptosis activation are interrelated in that TNF can stimulate neutral membrane sphingomyelinase, resulting in production of ceramide, which disrupts mitochrondrial electron transport, also eventually effecting release into the cytoplasm of mitochondrial cytochrome c. Cytochrome c plays a prominent early role in the signal transduction of caspase activation and cardiomyocyte apoptosis induced by reactive oxygen species. See, R. von Harsdord, et al., "Signaling pathways in reactive oxygen species-induced cardiomyocyte apoptosis," *Circ.,* 99:2934–2941, 1999. Production of reactive oxygen species is greatly enhanced as a consequence of ischemia-reperfusion of myocardium and oxidant stress produced during ischemia-reperfusion induces myocardial apoptosis. See, N. Maulik, et al., "Oxidative stress developed during the reperfusion of ischemic myocardium induces apoptosis," *Free Rad. Biol. Med,* 24:869–875, 1998. Thus, the activity of cytochrome c when it is transported to the cytoplasm appears to play an important and pivotal role in activating pro-apoptotic cascades, whether the initial induction of apoptosis is effected through membrane death receptor or mitochrondrial pathways.

In view of the foregoing it is readily apparent that there is a need for treatment of myocardial reperfusion injury that inhibits or prevents apoptosis.

SUMMARY OF THE INVENTION

It is therefore the general object of this invention to provides a method of inhibiting or preventing apoptosis in ischemic-reperfused myocardium using heparin or nonanticoagulant heparin.

The present invention provides a method for inhibiting apoptosis in ischemic-reperfused myocardium by administering to a mammal an effective amount of heparin to reduce myocardial cell death in myocardial infarction. It has been found that at doses greatly exceeding those needed for anticoagulation heparin substantially reduces reperfusion injury both in the isolated perfused heart and intact whole animal models of myocardial infarction. This protective effect is independent of heparin's activity as an anticoagulant.

In accordance with another aspect of this invention, there is provided a method for inhibiting apoptosis in ischemic-reperfused myocardium by administering to a mammal an effective amount of nonanticoagulant heparin, such as O-desulfated heparin, to reduce or prevent myocardial cell death in myocardial infarction.

In yet another aspect of this invention it was found that heparin or nonanticoagulant heparin when conjugated to a lipophilic moiety such as a fatty acid or cholesterol by reaction across a carboxylic acid or free amine group can be used to enhance cellular uptake by cell types not normally concentrating heparin, such as neurons, thereby enhancing the anti-apoptotic effect of heparin or nonanticoagulant heparin. Furthermore, heparin or nonanticoagulant heparin, either alone or conjugated to a lipophilic group, can be used to block apoptosis in situations of acute trauma, such as generalized trauma, global ischemia-reperfusion injury occurring as a consequence of hemorrhagic shock, or spinal cord injury, thereby preventing cell death in organs such as the spinal cord.

BRIEF DESCRIPTION OF THE DRAWINGS

Reference to the following detailed description may help to better explain the invention in conjunction with the drawings in which.

DETAILED DESCRIPTION OF THE INVENTION

The present invention now will be described more fully hereinafter with reference to the accompanying examples, in which preferred embodiments of the invention are shown. This invention may, however, be embodied in many different forms and should not be construed as limited to the embodiments set forth herein; rather these embodiments are provides so that this disclosure will be thorough and complete, and will fully convey the scope of the invention to those skilled in the art.

It has been fund that heparin in larger than usual anticoagulant doses of heparin and a variety of nonanticoagulant heparins (N-desulfated; 2-O, 3-O or 6-O desulfated; N-desulfated and reacetylated; and O-decarboxylated heparin) can attenuate ischemia-reperfusion injury in the heart and reduce myocardial infarct size as measured by the area of cellular necrosis and thus attenuate development of myocardial apoptosis. Examples of the preparation of O-desulfated nonanticoagulant heparin may be found in, for example, U.S. Pat. Nos. 5,668,118 and 5,912,237 incorporated herein by reference. "O-desulfated heparin" can include O-desulfated heparin having modifications, such as reduced molecular weight or acetylation, deacetylation, oxidation, and decarboxylation. The heparin or nonant:coagulant heparin may be given in amounts of 3 mg/kg to 100 mg/kg, but preferably in amounts from about 3.5 mg/kg to about 10 mg/kg.

Figure 1A:
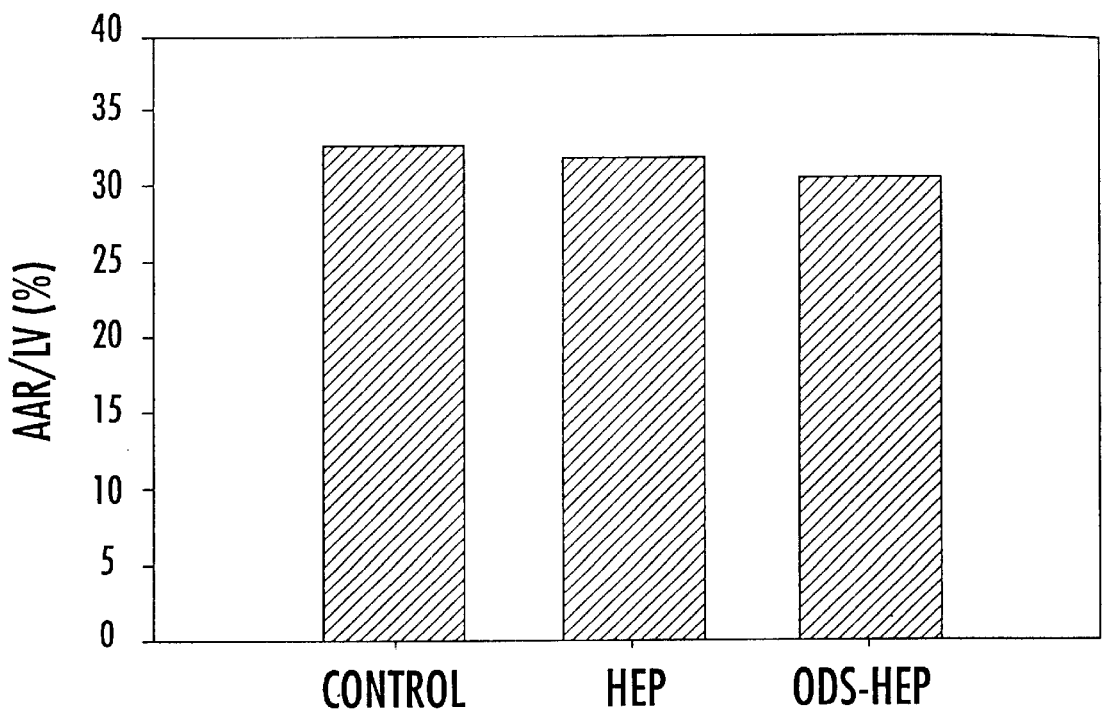
FIG. 1A is a graph showing that heparin and O-desulfated nonanticoagulant heparin treated hearts have identical risks for suffering injury or ratio of AAR to left ventricle (AAR/LV)
Figure 1B:
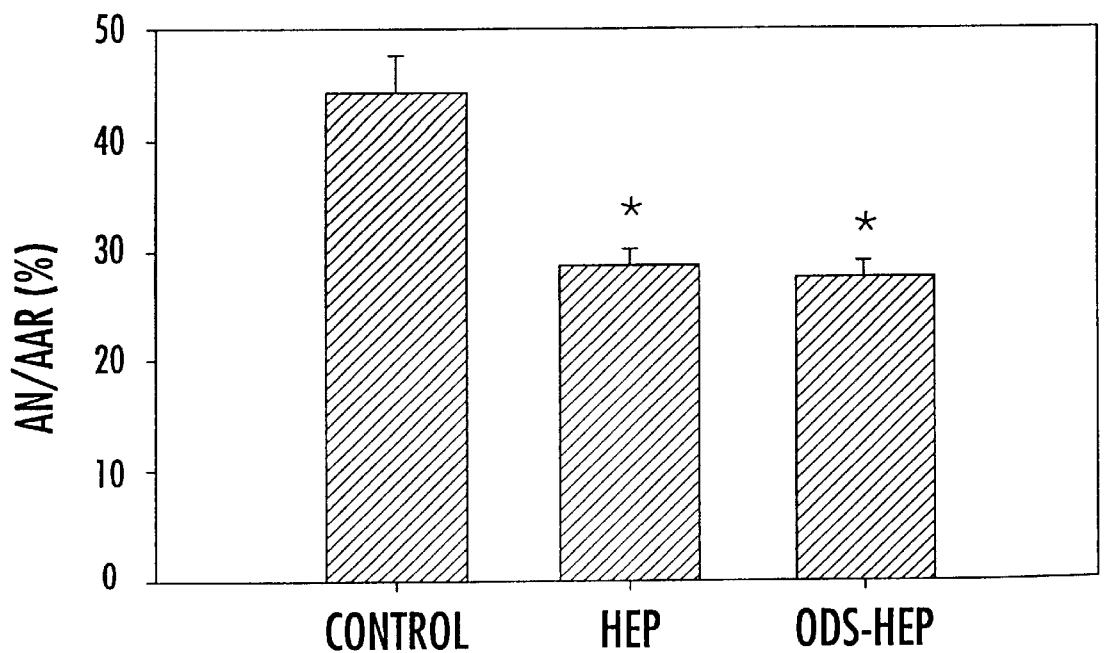
FIG. 1B is another graph showing that heparin and O-desulfated nonanticoagulant heparin reduce infarct size (AN/AAR) (or ratio of area of necrosis to area at risk)
Figure 2:
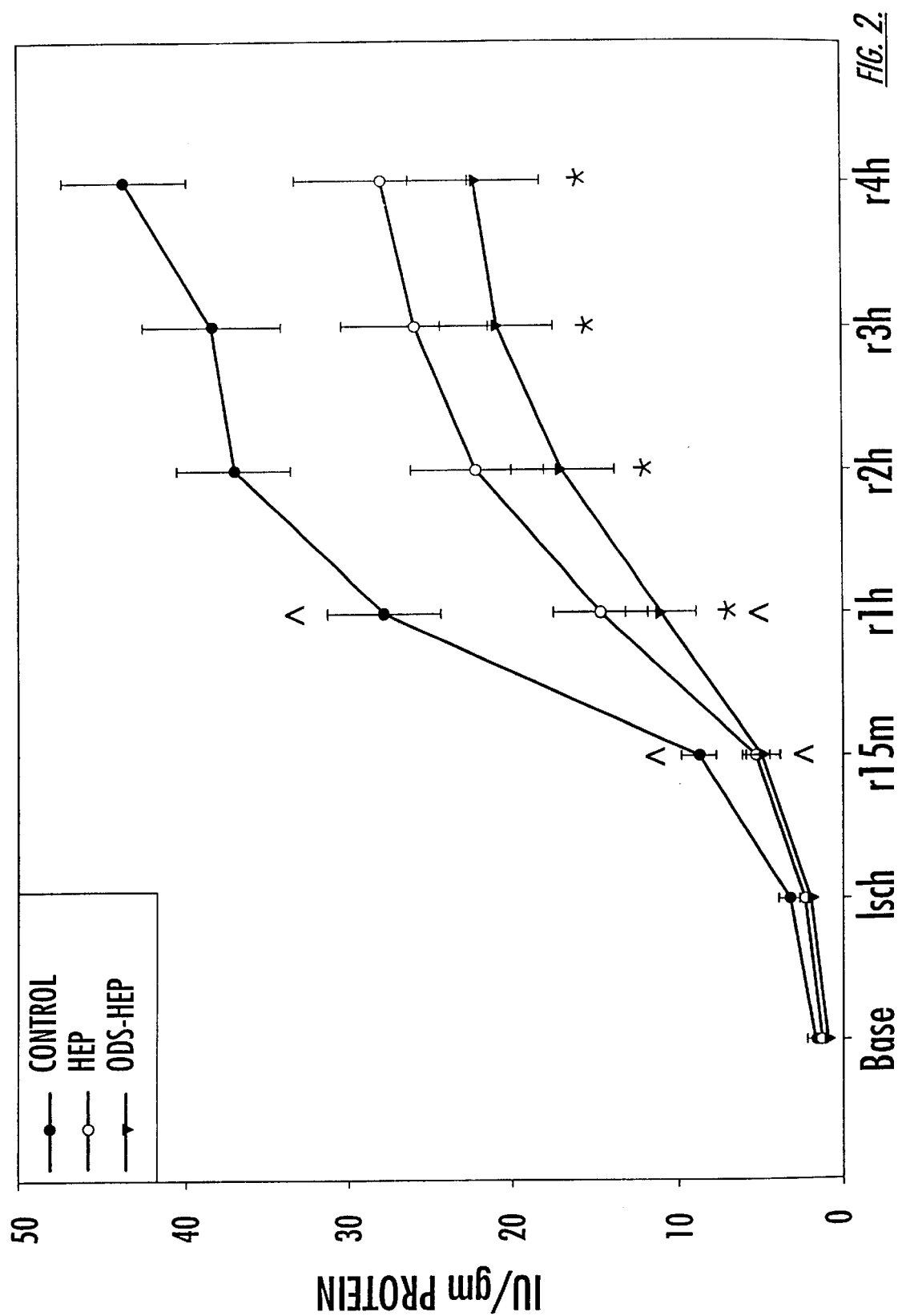
FIG. 2 demonstrates that heparin and O-desulfated nonanticoagulant heparin reduce plasma creatine kinase activity after infarction.
Figure 4:
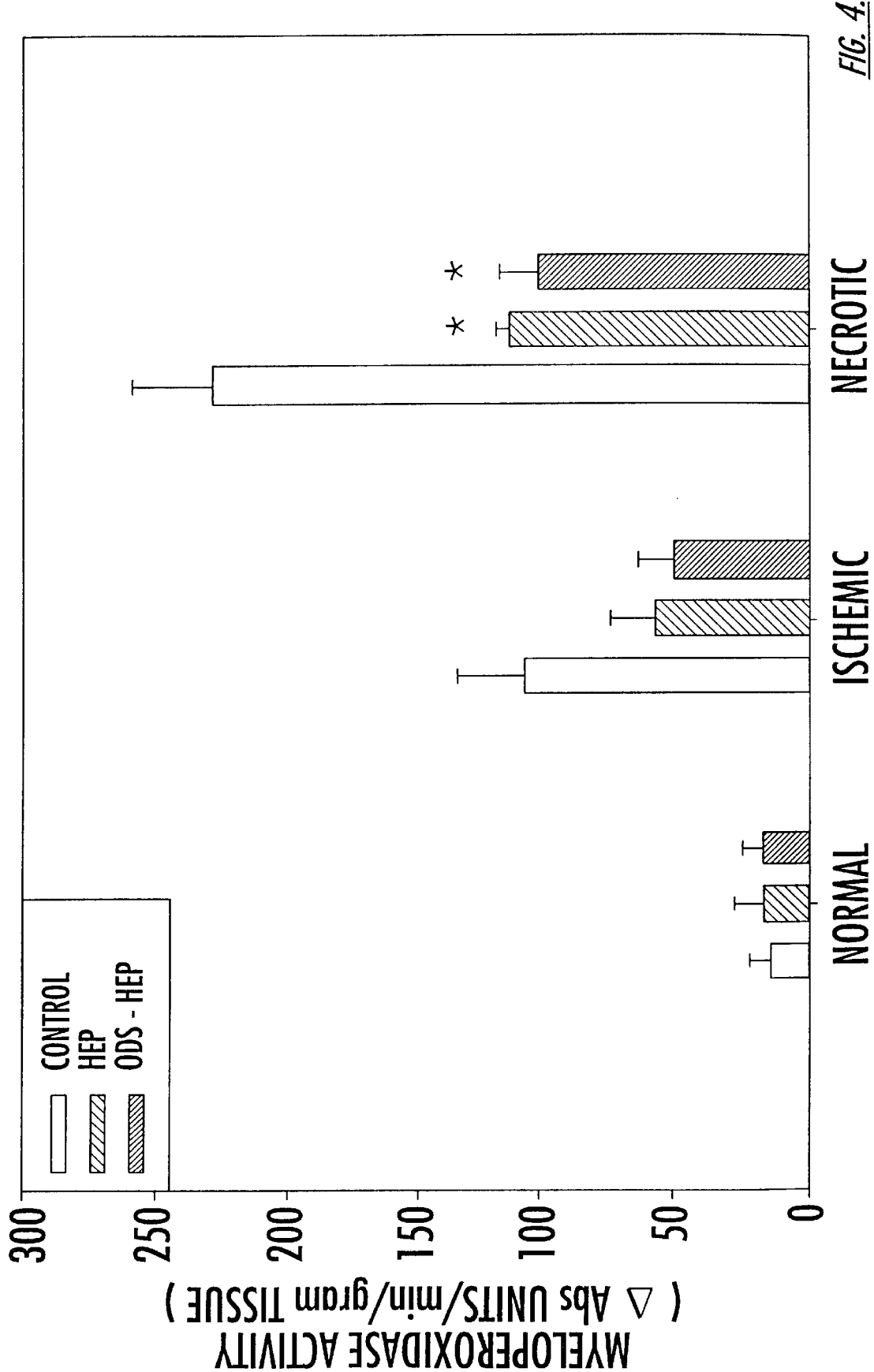
FIG. 4 demonstrates that heparin and O-desulfated nonanticoagulant heparin reduce influx of PMNs after myocardial infarction measured by activity of TMN specific enzyme myeloperoxidase in myocardial tissue.
Figure 5:
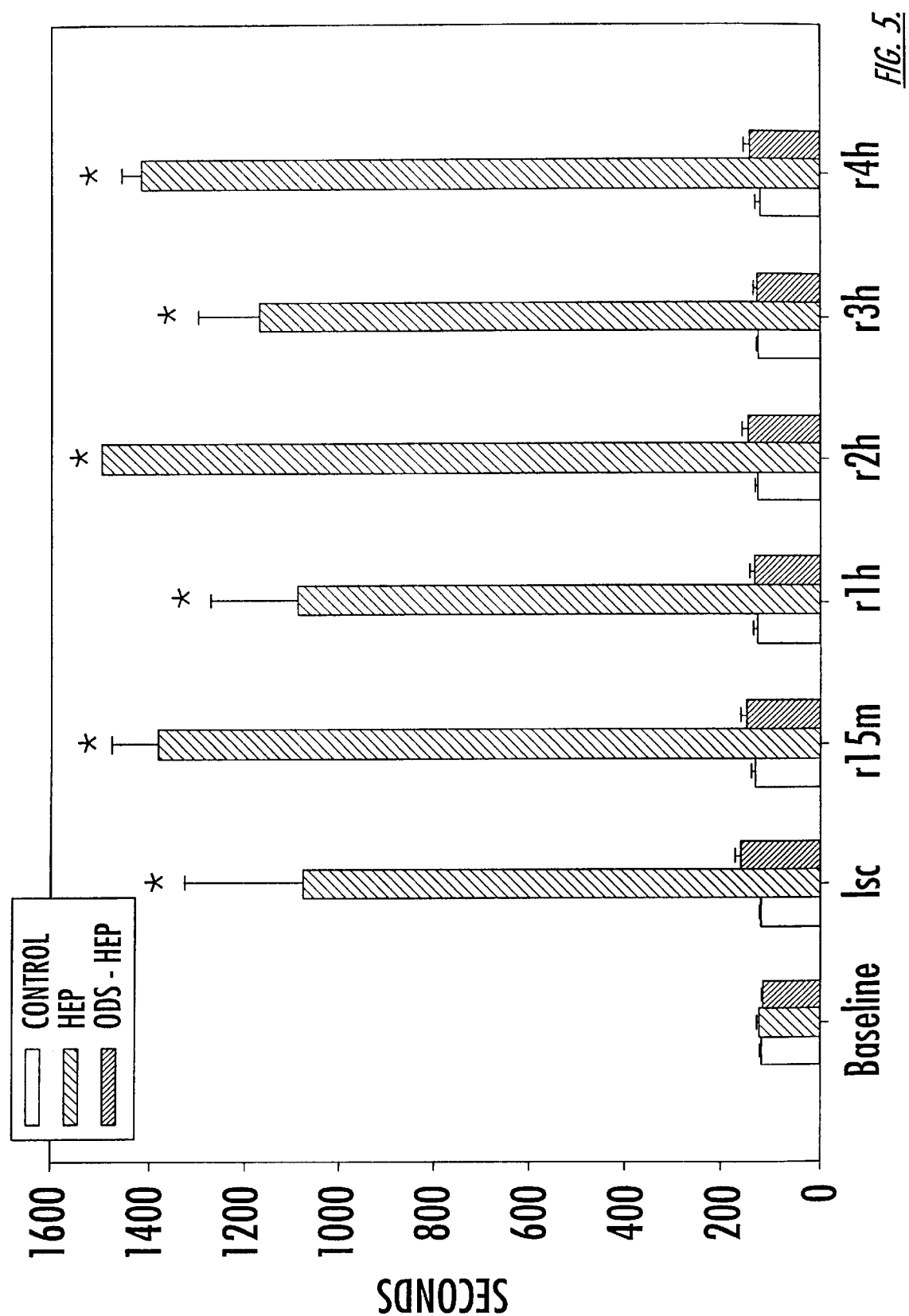
FIG. 5 shows that O-desulfated nonanticoagulant heparin did not produce anticoagulation in vivo measured by ACT (activated clotting time)
Figure 6:
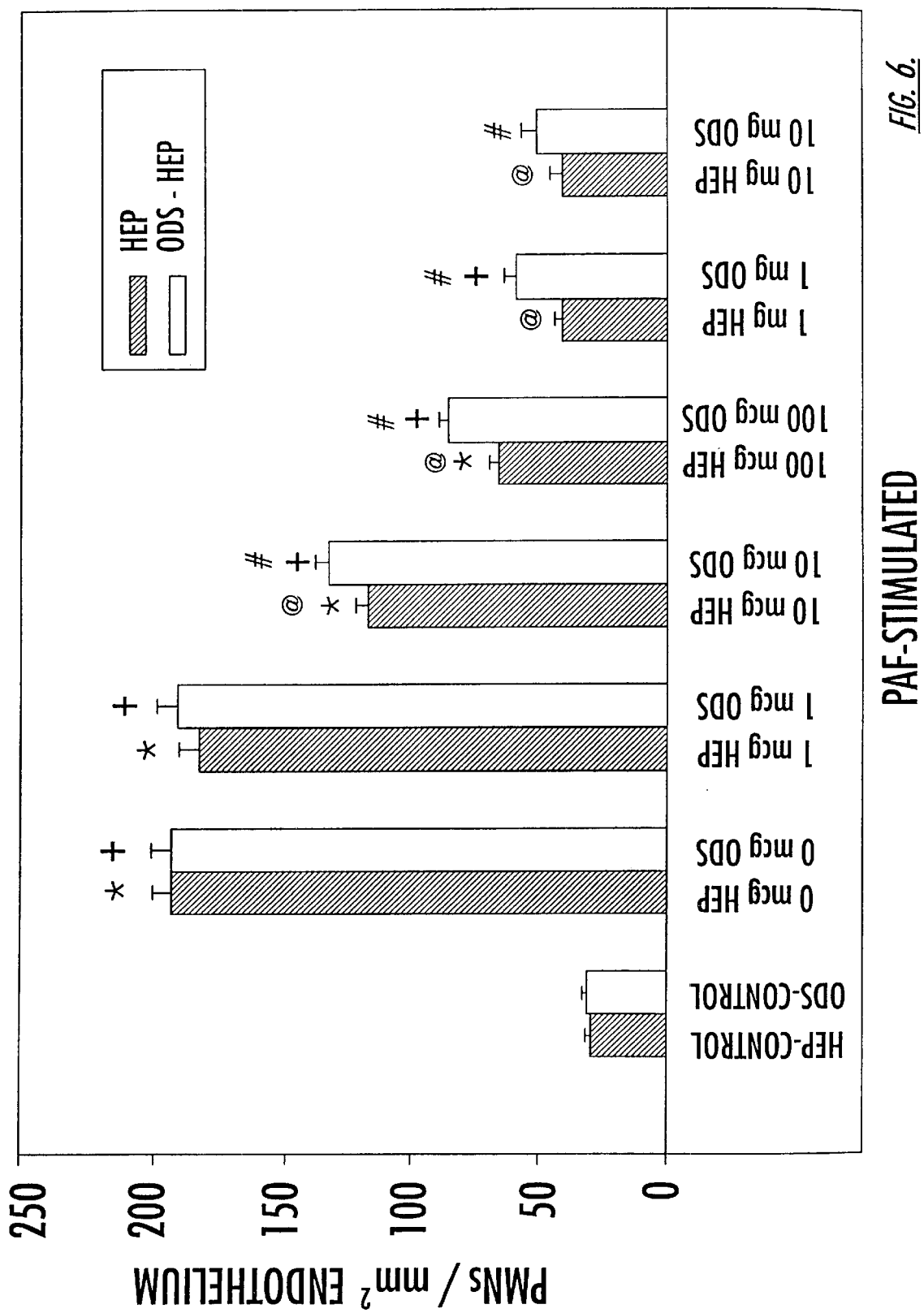
FIG. 6 demonstrates that heparin and partially O-desulfated nonanticoagulant heparin block PMN adherence to normal coronary artery endothelium in vitro.
Figure 7:
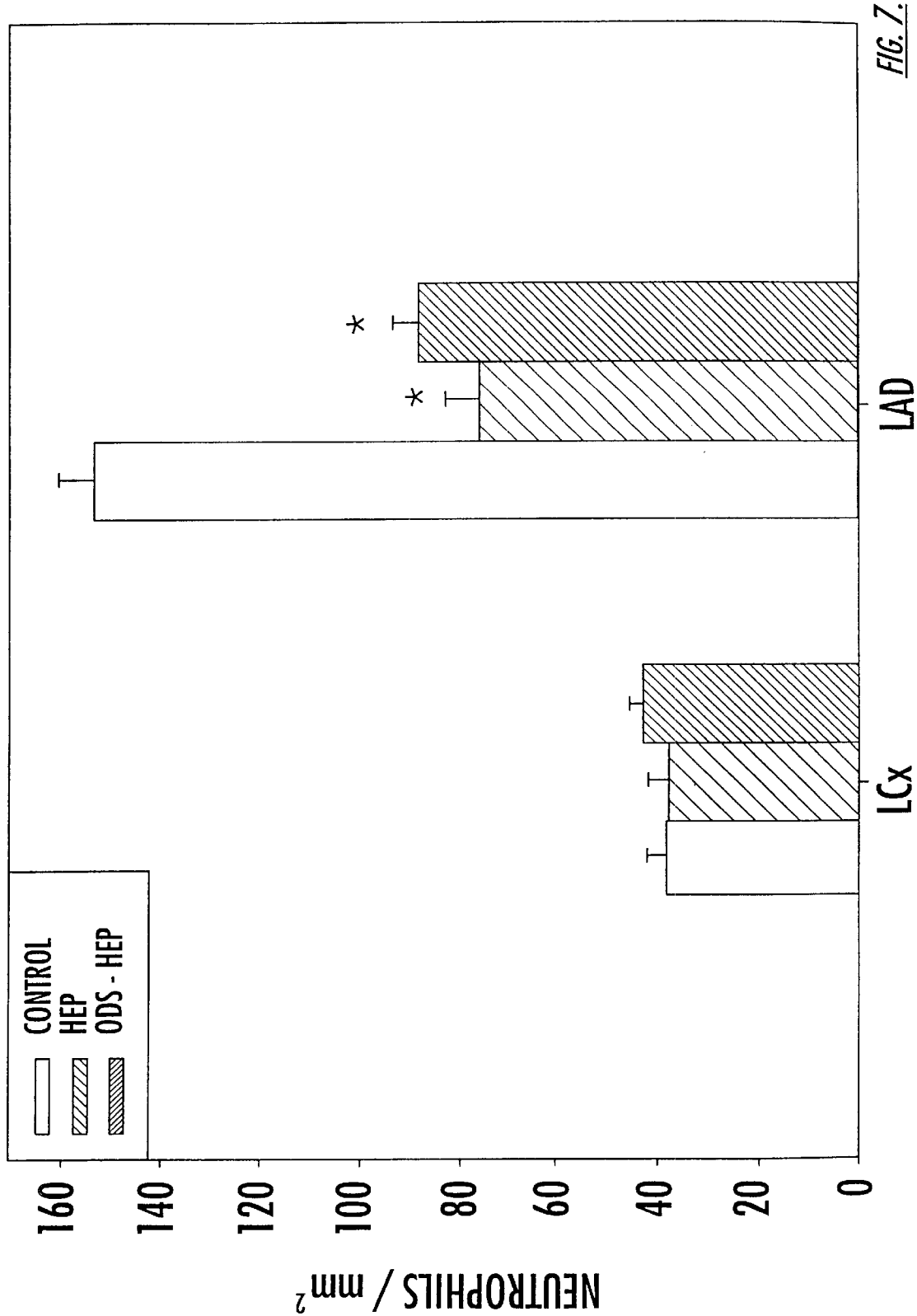
FIG. 7 illustrates that heparin and O-desulfated nonanticoagulant heparin reduce PMN adherence to post-experimental coronary artery endothelium.
Figure 8:
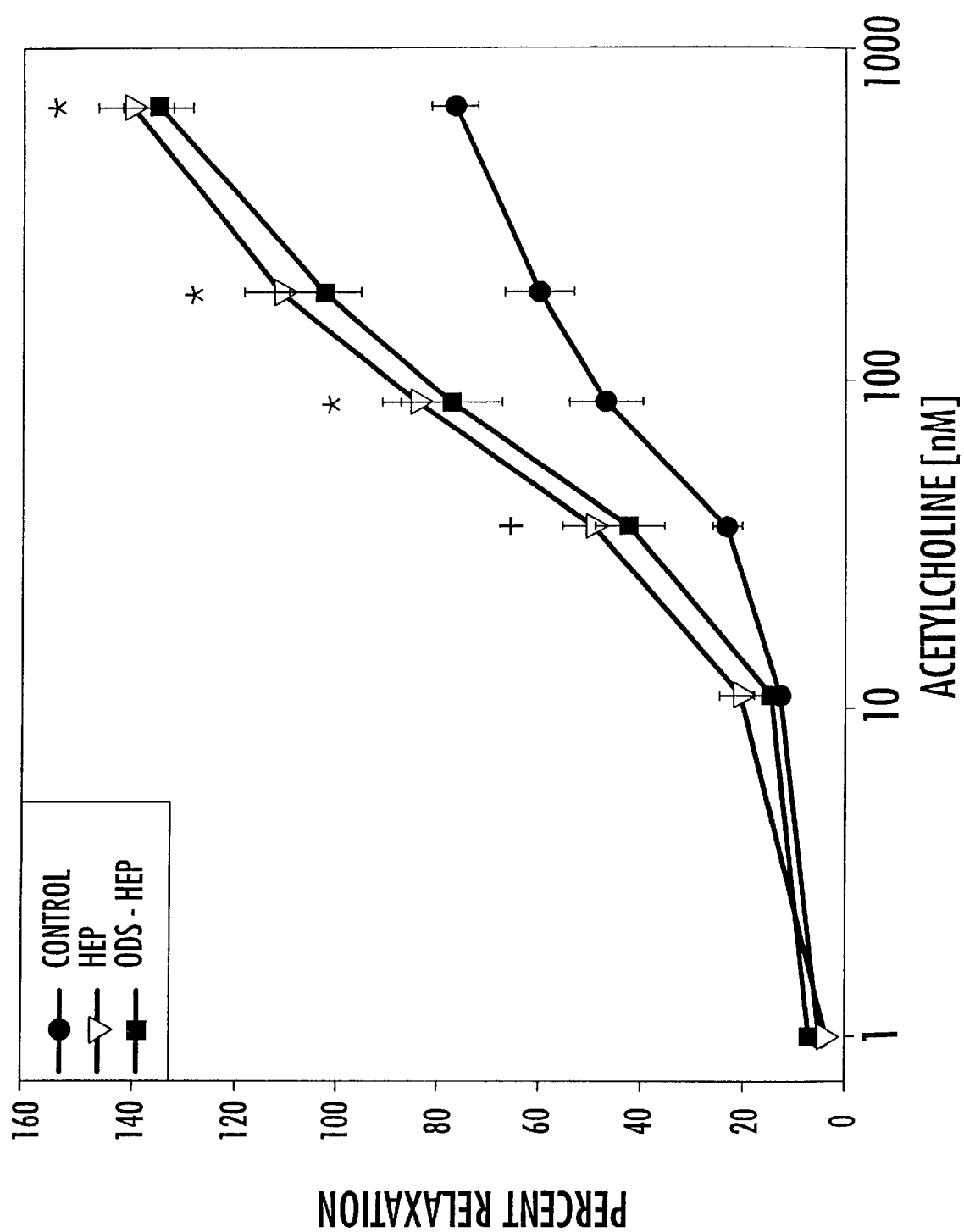
FIG. 8 shows that heparin and O-desulfated nonanticoagulant heparin preserve the vasodilator function of ischemic-reperfused coronary arteries.

The mechanisms by which heparin reduces reperfusion injury, were studied by in vivo ischemia-reperfusion in a canine infarct model using partially O-desulfated nonanticoagulant heparin (ODS-HEP). Despite greatly reduced anti-complement activity, ODS-HEP decreases PMN adherence to coronary epithelium. This was found both in vitro when stimulated by PAF (FIG. 6) and in vivo when stimulated by coronary ischemia and reperfusion (FIG. 7). Given at the time of reperfusion, ODS-HEP decreases PMN influx into ischemic-reperfused myocardium (FIG. 4) and reduces infarct size (FIGS. 1 and 2). Depressed contractile function remained initially unchanged, but function might be expected to recover over time as stunned but not irreversibly injured myocardium recovers to a normal energy state following ischemia. ODS-HEP also preserves normal vasodilator function in ischemic-reperfused coronary endothelium (FIG. 8). These benefits were produced without anticoagulation (FIG. 5).

Infiltration of PMNs plays a critical role in producing myocardial reperfusion injury. See, T. Yamszaki, et al., "Expression of intercellular adhesion molecule-1 in rat heart with ischemia/reperfusion and limitation of infarct size by treatment with antibodies against cell adhesion molecules," Am. J Pathol., 143:410–418, 1993; and P. J. Simpson, et al., "Reduction of experimental canine myocardial reperfusion injury by a monoclonal antibody (anti-Mo1, andti-CD11b)

that inhibits leukocyte adhesion," *J. Clin. Invest.* 81:625–629, 1988. One of the earliest events mediating PMN influx from ischemia and reperfusion is the increase in surface expression of various endothelial cell adhesion molecules (ECAMs), including intercellular adhesion molecule-1 (ICAM-1), E-selectin and P-selectin, which increase rolling and adhesion of PMNs to coronary endothelium. See, T. Yamszaki, et al., supra. Enhanced expression of adhesion molecules during ischemia-reperfusion is result of the activation of nuclear factor-κB (NF-κB), See, T. Yamszaki, et al., supra, which promotes expression of many inflammatory and immune response genes. NF-κB is cytosolic when complexed with its inhibitor, IκB, but is activated by phosphorylation, ubiquitination and proteolytic degration of IκB. I. Stancovski, et al., "NF-κB activation: the IκB kinase revealed?," *Cell,* 91:299–302, 1997. Release from IκB exposes the NF-κB nuclear localization sequence (NLF), a highly cationic domain of eight amino acids (VQRDRQKLM, single-letter amino acid code) that targets nuclear translocation. Y.-Z. Lin, et al., "Inhibition of nuclear translocation of transcription fractor NF-κB by a synthetic peptide containing a cell membrane-permeable motif and nuclear localization sequence," *J. Biol. Chem.,* 270:14255–14258, 1995; and S. T. Malek, et al., "IκBα functions through direct contacts with the nuclear localization signals and the DNA binding sequences of NF-κB," *J. Biol. Chem.,* 273:25427–25435, 1998. NF-κB is activated in the heart and cultured myocytes by ischemia or ischemia and reperfusion, C. Li, et al., "Early activation of transcription factor NF-κB during ischemia in perfused rat hearts," *Am. J. Physiol,* 276 (*Heart Circ. Physiol.* 45):H543–H552, 1999; and R. Kacimi, et al., "Expression and regulation of adhesion molecules in cardiac cells by cytokines, response to acute hypoxia," *Circ. Res.* 82:576–586, 1998, with subsequent upregulation of adhesion molecules on the myocyte surface. See, R. Kacimi, et al., supra. Nuclear translocation of NF-κB is prevented by synthetic permeable peptides containing the NF-κB NLF, which competes for nuclear uptake. See, Y.-Z. Lin, et al., supra. Heparin is readily bound and internalized into the cytosolic compartment by endothelium, vascular and airway smooth muscle, mesangial cells and even cardiac myocytes. T. C. Wright, et al., "Regulation of cellular proliferation by heparin and heparin sulfate. In Lane DA, Lindahl U, eds. *Heparin Chemical And Biological Properties, Clinical Applications.* Boca Raton, Fla.:CRC Press, Inc. 1989, p.295–316; and H. Akimoto, et al., "Heparin and heparin sulfate block angiotensin-II-induced hypertrophy in cultured rat cardiomyocytes. A possible role of intrinsic heparin-like molecules in regulation of cardiomyocyte hypertrophy," *Circulation,* 93:810–816, 1996.

Figure 9A:
FIG. 9A demonstrates that NF-κB (brown stained) is normally present in the cytoplasm of unstimulated human umbilical vein endothelial cells (HUVECs) and that heparin and O-desulfated nonanticoagulant heparin prevent translocation of NF-κB from cytoplasm to the nucleus.
Figure 9B:
FIG. 9B shows HUVEC stimulated with TNFα without addition heparin. Some, but not all nuclei now stain positive for anti-p65, corresponding to translocation of NF-κB from cytoplasm to the nucleus in HUVEC pre-treated with 200 μg/ml O-desulfated nonanticoagulant heparin.
Figure 9C:
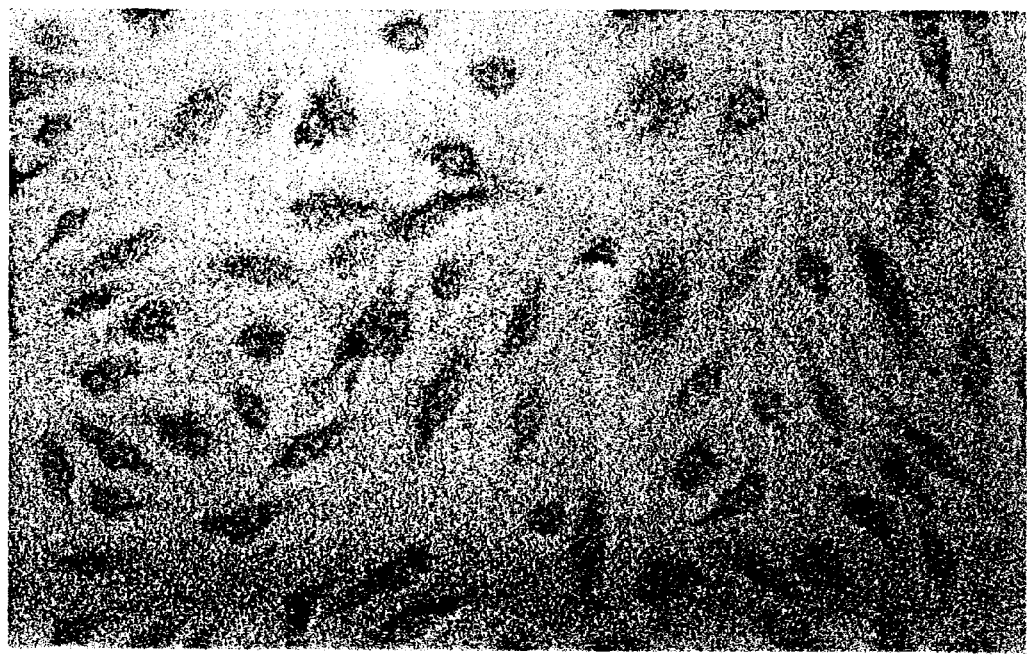
FIG. 9C shows TNF stimulation fails to produce anti-p65 nuclear staining and activation of NF-κB HUVECs pre-treated with O-desulfated nonanticoagulant heparin.
Figure 10:
FIG. 10 are electrophoretic mobility shift assays showing that O-desulfated nonanticoagulant heparin decreases DNA binding of NF-κB in TNF-stimulated FIG. 11A are electrophoretic mobility shift assays of nuclear protein from ischemic-reperfused rat myocardium O-desulfated nonanticoagulant heparin showing decreases in DNA binding of NF-κB in ischemic-reperfused myocardium.

It was found that the polyanion heparin binds electrostatically to the positively charged amino acids of the NLF and prevent it from targeting NF-κB to the nuclear pore. Heparin and O-desulfated nonanticoagulant heparin prevented TNF-induced endothelial cell translocation of NF-κB from cytoplasm to the nucleus, studied immunohistochemically (FIG. 9), and reduced binding of NF-κB to DNA in electrophoretic mobility shift assays performed with HUVEC nuclear protein (FIG. 10). ODS heparin also prevented enhanced DNA binding of NF-κB in ischemic-reperfused myocardium (FIG. 11). Thus, inhibition of NF-κB activation appears specific for heparin. These results are consistent with the possibility that heparin electrostatically blocks the NLF, exposed when NF-κB dissociates from its inhibitor IκB.

Heparin and nonanticoagulant heparin prevent myocardial apoptosis by three mechanisms:

1. Inhibition of Endogenous TNF Production by Myocardium

Decreasing endogenous production of TNF by myocardium itself would reduce the amount of hormone locally available to attach to TNFR1 receptors and stimulate death domain-dependent induction of apoptosis in an autocrine fashion. TNF expression is heavily regulated by the transcription factor nuclear factor-κB. See, F. G. Wulczyn, et al., "The NF-κB and I κB gene families: mediators of immune response and inflammation," *J. Mol. Med* 74:749–769, 1996.

Heparin in higher than anticoagulant doses or nonanticoagulant heparin both inhibit NF-κB activation in myocardium. See, V. H. Thournai, supra. In myocardial tissue samples from the isolated perfused rat hearts studied in the above publication, we measured myocardial TNF levels after 10 minutes ischemia and 30 minutes reperfusion. TNF levels in nonanticoagulant heparin treated ischemic-reperfused hearts were only 30% of those in untreated, ischemic reperfused hearts, reducing the potential stimulus for TNFR1 mediated apoptosis (5.74±1.65 for ischemic-reperfused hearts vs 1.78±0.61 pg/g dry weight for nonanticoagulant heparin treated ischemic-reperfused hearts, p<0.05).

2. Reduction of Exogenous TNF Production by Reduction of Inflammatory Cell Influx into Ischemic-reperfused Myocardium It has been also demonstrated that larger than anticoagulant doses of heparin and nonanticoagulant heparin reduce the influx of inflammatory cells into ischemic-reperfused myocardium. V. H. Thournai, supra. Blood inflammatory elements such as neutrophils and macrophages are rich sources of TNF production, and apoptotic myocardial cell death is highly correlated with inflammatory cell influx into myocardium following ischemic and reperfusion. See, D. Velez, et al., "Inflammatory cell infiltration and apoptotic cell death after myocardial ischemia and reperfusion," *Circ.* 100 (Supplement):I-691, 1999. Thus, inhibition of inflammatory cell influx should reduce exogenous TNF available to induce TNFR1 death domain mediated apoptotis of following myocardial infarction.

3. Direct Inhibition of Cytochrome c Mediated Activation of Apaf-1

The activation of Apaf-1, enabling it to convert procaspase 9 to its own active form requires binding to cytochrome c. It is the lack of availability of cytochrome c within normal cytoplasm that prevents activation of this pathway of apoptosis. Events which increase the permeability of the outer mitochondrial membrane, allowing flux of cytochrome c out into the cytoplasm, are the initiating events for mitochrondrial regulated cell death. The entire anti-apoptotic Bcl-2 family and pro-apoptotic Bax and BH3 families of proteins regulate apoptosis by blocking (Bcl-2) or opening (Bax and BH3) pores in the mitochondrial membrane through which cytochrome c might flux outward. See, J. M. Adams, et al., "The Bcl-2 protein family:arbiters of cell survival," *Science* 281:1322–1326, 1998. Thus, cytochrome c performs a pivotal function in initiating the cellular apoptosis cascade.

Mitochrondrial cytochrome c is a basic protein with a positive charge of +9.5 at neutral pH. See, L. C. Petersen, et al., "The effect of complex formation with polyanions on the redox properties of cytochrome c," *Biochem. J.,* 192:687–693, 1980; Bagelova, et al., "Studies on cytochrome c-heparin interactions by differential scanning calorimetry," *Biochem. J.,* 297:99–101. 1994. Within the cell, cytochrome c forms complexes with its natural electron chain redox partners such as cytochrome bc1 complex and cytochrome c oxidase. These complexes are electrostatic in nature and involve charge-dependent binding to the positive lysine residues surrounding the exposed edge of the "haem moiety" to negatively charged amino acids on its respiratory chain partners. It is this haem-edge area on the cytochrome c molecule that is also involved in the exchange of electrons with its natural redox partners and the site of reaction with small molecules such as the reducing agent ascorbate. Thus, the cytochrome c molecule electrostatically binds in the same region as it is functionally active in redox reactions.

Because of its positive charge, cytochrome c naturally binds to other polyanions such as heparin and dextran sulfate. See, L. C. Petersen, et al., supra. Binding of cytochrome c to heparin greatly decreases its reactivity in redox reactions. An example is the 200 fold reduction in reaction with ascorbate effected by addition of 40 $\mu$g/ml heparin to 10 $\mu$M cytochrome c and 0.4 M sodium ascorbate in 10 mM Tris buffer, pH 7.4 (see Table 2, Peterson, et al., cited above). The complex of heparin and cytochrome c occurs whether cytochrome c is in the reduced or oxidized state. See, M. Antalik, M., et al., "Spectrophotometric detection of the interaction between cytochrome c and heparin," Biochem. Biophys, Acta 1100:155–159, 1992). Heparin is readily taken up and internalized by endothelium, smooth muscle. See, T. C. Wright, et al, "Regulation of cellular proliferation by heparin and heparin sulfate." Heparin. Chemical and Biological properties. Clinical applications, D. A. Lane and U. Lindahl, editors, CRC Press, Inc., Boca Raton, Fla., 295–316. Heparin is readily taken up and internalized by myocardium. See, H. Akimoto, et al., "Heparin and heparin sulfate block angiotensin-II-induced hypertrophy in cultured neonatal rat cardiomyocytes. A possible role of intrinsic heparin-like molecules in regulation of cardiomyocyte hypertrophy," Circ, 93:810–816, 1996.

It has been shown that heparin and nonanticoagulant heparin inhibits activation of nuclear factor-$\kappa$B in cultured human umbilical vein endothelial cells and in whole ischemic-reperfused rat hearts. In its unactivated state, nuclear factor-$\kappa$B is a cytosolic protein. Therefore, at doses higher than used for anticoagulation, heparin or nonanticoagulant heparin both concentrates in myocardial endothelium and myocardium itself in levels sufficient to affect cytosolic events.

Positively charged cytochrome c binds to Apaf-1 on a negatively charged region of the Apaf-1 molecule characterized by 12 WD (tryptophan-aspartic acid) amino acid repeats. See, H. Zou, et al., "Apaf-1, a human protein homologous to C. elegans CED-4, participates in cytochrome c-dependent activation of caspase-3," Cell, 90:405–413, 1997. Because the 6 aspartic acids are all acidic, this is a very negatively charged region of the Apaf-1 molecule that likely binds to the same positively charged lysine residues adjacent to the haem edge region, where cytochrome c binds other negatively charged partners. Binding of positively charged cytochrome c to the negatively charged 12 WD repeat region of Apaf-1 induces conformational changes that allow Apaf-1 to bind, in turn, to caspase-9 and activate it. See, J. C. Reed, "Cytochrome c: Can't live with it—Can't live without it," Cell, 91:559–562, 1997. As strong polyanions, heparin or nonanticoagulant heparin would naturally compete with cytosolic Apaf-1 for binding to positively charged cytochrome c. Electrostatic interaction with proteins is the basis for other inhibitory effects of heparin, such as the ability of heparin and other sulfated polysaccharides to inhibit the positively charged granular neutrophil proteases human leukocyte elastase and cathepsin G. See, N. V. Rao, et al., "Sulfated polysaccharides prevent human leukocyte elastase-induced lung injury and emphysema in hamsters," Am. Rev. Respir. Dis, 142:407–412, 1990. By binding any cytochrome c entering the cytoplasm, heparin or nonanticoagulant heparin would prevent the interaction of cytochrome c with Apaf-l, and thereby prevent procaspase-9 activation leading to apoptotis.

This activity of heparin or nonanticoagulant heparin to inhibit apoptosis would not be predicted based upon current knowledge. Ischemic preconditioning, or exposure of the heart to short noninjurious periods of ischemia, has been found to decrease apoptosis as a result of longer periods of ischemia and reperfusion. See, C. A. Piot, et al., Circ., 96:1598–1604, 1997. Nuclear factor-$\kappa$B plays an essential role in myocardial ischemic preconditioning. See, Y-T Zuan, et al., "Nuclear factor-$\kappa$B plays an essential role in the late phase of ischemic preconditioning in conscious rabbits," Circ. Res, 84:1095–1109, 1999. Nuclear factor-$\kappa$B has also been reported to be essential in preventing apoptosis from TNF. See, A. A. Beg, et al., "An essential role for NF-$\kappa$B in preventing TNF-$\alpha$-induced cell death," Science, 274:782–784, 1996; and C. Y. Wang, et al., "TNF- and cancer therapy induced apoptosis: potential by inhibition of NF-$\kappa$B," Science, 274:784–789, 1996. Thus, because, it has been shown that heparin or nonanticoagulant heparin inhibit NF-$\kappa$B, the prior art would suggest that heparin or nonanticoagulant heparin would also reduce the anti-apoptotic effects of NF-$\kappa$B and have the overall effect of enhancing apoptosis.

The strategy of using high doses of heparin or nonanticoagulant heparin to inhibit apoptosis will also have benefit in the treatment of stroke. Recent evidence points to the fact that as many as 50% of neurons that are lost as a consequence of stroke are dying by the process of apoptosis. See, M. Baringa, "Stroke-damaged neurons may commit cellular suicide," Science, 281:1302–1303, 1998; and J-M. Lee, et al., "The changing landscape of ischemic brain injury mechanisms," Nature, 399 (Supplement): A7–A14, 1999.

Recently, activation of NF-$\kappa$B has been shown to play an essential role in ischemic preconditioning. While possibly related to anti-apoptotic genes induced by NF-$\kappa$B, ischemic preconditioning bears similarity to the tolerance against lethal endotoxemia conferred by prior exposure to sublethal doses of lipopolysaccharide. Tolerance to endotoxin induces several events which negatively regulate subsequent NF-$\kappa$B activation. First, endotoxin related NF-$\kappa$B activation induces transcriptional upregulation of I$\kappa$B-$\alpha$ and p105, trapping NF-$\kappa$B in the cytoplasmic compartment. See, C. Stratowa, et al., "Transcriptional regulation of the human intercellular adhesion molecule-1 gene: a short review," Immunobiol. 193:293–304, 1995. Second, increased production of p105 also leads to enhanced formation of p50 homodimers, which lack transcription-activation domains but compete with active Rel proteins at NF-$\kappa$B binding sites. See, T. S. Blackwell, et al., "the role of nuclear factor-$\kappa$B in cytokine gene regulation," Am. J Respir. Cell Miol. Biol., 17:3–9, 1997. Finally, endotoxin tolerance is associated with depletion of latent cytoplasmic p65 containing NF-$\kappa$B heterodimers in tolerant cells. See, T. S. Blackwell, et al., "Induction of endotoxin tolerance depletes nuclear factor-$\kappa$B and suppresses its activation in rat alveolar macrophages," J. Leukoc. Biol., 62:885–891, 1997. These events would also be expected from NF-$\kappa$B activation by sublethal ischemia, providing an explanation for how NF-$\kappa$B can mediate both protection from short periods of ischemic preconditioning and injury from more prolonged ischemia with reperfusion related infarction.

When given at the time of coronary reperfusion, nonanticoagulant heparin decreases myocardial infarct size, reduces neutrophilic influx into necrotic myocardium and preserves endothelial vasodilator function within the ischemic-reperfused coronary artery at risk without producing anticoagulation. Inhibition of NF-κB activation and myocardial reperfusion injury is unlikely from the previously reported anti-complement activity of heparin, since the nonanticoagulant heparin we used has low inhibitory activity against complement. These findings provide new insight into the mechanisms of anti-inflammatory activity of heparin, and disclose a true nonanticoagulant heparin with potential for interrupting both the pathophysiologic consequences of ischemia-reperfusion syndromes and NF-κB mediated inflammation.

The present invention is more particularly described in the following examples which are intended as illustrative only, since numerous modifications and variations therein will be apparent to those skilled in the art.

EXAMPLE 1

The materials used in the examples were as follows: Acetylcholine chloride, the calcium ionophore A23187, sodium nitroprusside, and indomethacin (Sigma, St. Louis, Mo.), and U-46619 (Upjohn, Kalamazoo, Mich.) were used in concentrations shown by H. Sato, et al., "L-arginine inhibits neutrophil adherence and coronary artery dysfunction," *Cardiovasc. Res.,* 31:63–72, 1996. Grade I-A heparin sodium salt from porcine intestinal mucosa (Sigma) was resuspended with Krebs-Henseleit (K-H) buffer and administered as an intravenous bolus (3 mg/kg to dogs). Partially O-desulfated nonanticoagulant heparin (ODS-HEP) was synthesized by reduction with sodium borohydride followed by lyophilization under the conditions taught in A. Fryer, et al., "Selective O-desulfation produces nonanticoagulant heparin that retains pharmacologic activity in the lung," *J. Pharmacol. Exp. Therap.,* 282:208–219, 1997.(12). The resulting heparin derivative was a partially 2-O and 3-O desulfated heparin of approximately 10,500 daltons with an anticoagulant activity of 7.7±0.9 U/mg in the USP assay and 4.9±0.8 U/ml anti-Xa activity in the amidolytic assay, compared to 170 USP/mg anticoagulant activity and 150 U/mg anti-Xa activity for the unmodified porcine intestinal heparin from which it was manufactured. See, A. Fryer, supra. While 1.0 mg/ml of unmodified heparin inhibited 91±2% of the lysis of human red cells by canine plasma, ODS-HEP reduced erythrocyte lysis only by 4±2% at 1.0 mg/ml. ODS-HEP was resuspended K-H buffer and administered as an intravenous bolus (3 mg/kg to dogs; 6 mg/kg to rats, with 100 μg/ml added to K-H perfusate for isolated hearts).

EXAMPLE 2

This example sets forth the in vivo studies that were performed.
Surgical Procedure All animals were handled in compliance with the "Guide for the Care and Use of Laboratory Animals" published by the National Institutes of Health (NIH Publication No. 85-23, revised 1985). The Institutional Animal Care and Use Committees of Emory University and Carolinas Medical Center approved the study protocols.

Twenty-four heartworm-free adult dogs of either sex were anesthetized with sodium pentobarbital (20 mg/kg) and endotracheally intubated. Anesthesia was supplemented with fentanyl citrate (0.3 μg/kg/min) and diazepam (0.03 μg/kg/min) administered intravenously as needed to maintain deep anesthesia. Each dog was ventilated with a volume-cycled respirator using oxygen-enriched room air. A rectal temperature probe was inserted to measure core body temperature. The right femoral artery and vein were cannulated with polyethylene catheters for arterial blood sampling and for intravenous access, respectively. Serial arterial blood gases were measured to maintain the arterial oxygen tension greater than 100 mmHg. Arterial carbon dioxide tension was maintained between 30 and 40 mmHg, and arterial pH was maintained between 7.35 and 7.45 by adjustment of the ventilatory rate, and acidemia was counteracted with intravenous sodium bicarbonate.

After median sternotomy, the superior and inferior vena cava were looped with umbilical tapes and the heart suspended using a pericardial cradle. Millar catheter-tipped pressure transducers (Millar Instruments, Houston, Tex.) were placed in the proximal aorta and in the left ventricular cavity to measure aortic and left ventricular pressure, respectively. A polyethylene catheter was inserted into the left atrium for colored microsphere injection. A one centimeter portion of the left anterior descending (LAD) coronary artery distal to the first diagonal branch was dissected and loosely encircled with a 2-0 silk suture. A pair of opposing ultrasonic crystals were placed intramyocardially within the proposed ischemic area at risk within the left anterior descending coronary artery distribution, and were used to assess regional function within the area at risk. See, J. E. Jordan, et al., "Adenosine $A_2$ receptor activation attenuates reperfusion injury by inhibiting neutrophil accumulation, superoxide generation and coronary adherence," *J. Pharm. Exp. Therap.,* 280:301–309, 1997.

Experimental Protocol

The dogs were randomized to one of three groups (n=8 in each group): 1) Control (saline), 2) unmodified heparin (HEP, 3 mg/kg) and 3) modified heparin (ODS-HEP, 3 mg/kg). The LAD was occluded for 90 min producing ischemia and then released for four hours of reperfusion. Each pharmaceutical agent (saline, HEP, ODS-HEP) was infused as an intravenous bolus 10 minutes prior to initiation of reperfusion and at 90 minutes and 180 minutes during reperfusion. Analog hemodynamic and cardiodyamic data were sampled by a personal computer using an analog-to-digital converter (Data Translation, Marlboro, Mass.), as described previously in J. E. Jordan, et al., supra. Hemodynamic and cardiodynamic data were averaged from no fewer than 10 cardiac cycles. Percent systolic shortening, segmental work, and the characteristics of segmental stiffness described by exponential curve-fitting analysis were determined as described. J. E. Jordan, et al., supra. Activated clotting time (ACT, in seconds) was measured throughout the experiment using the Hemochron 401 Whole Blood Coagulation System (International Techidyne, Edison, N.J.). Arterial blood creatine kinase activity was analyzed using a kit from Sigma Diagnostics and expressed as international units per gram of protein. J. E. Jordan, et al., supra. The experiment was terminated with a bolus of intravenous sodium pentobarbital (100 mg/kg). The heart was immediately excised for further analysis and placed into ice-cold Krebs-Henseleit (K-H) buffer of the following composition: 118 mM NaCl, 4.7 mM KCl, 1.2 mM $KH_2PO_4$, 1.2 mM $MgSO_4$ $7H_2O$, 2.5 mM $CaCl_2$ 2 $H_2O$, 12.5 mM $NaHCO_3$, and 11 mM glucose at pH 7.4.
Determination of Area at Risk, Infarct Size and Regional Myocardial Blood Flow After postexperimental excision of the heart, the myocardial area at risk and infarct size were determined as previously described using Unisperse pigment exclusion and 1% triphenyltetrazolium chloride, respectively. J. E. Jordan, et al., supra. The area at risk (AAR) and infarct size were calculated gravimetrically as previously described in J. E. Jordan, et al., supra. Regional myocardial blood flow in the ischemic-reperfused and non-ischemic myocardium were obtained by spectrophotometric analyses of dye-release colored microspheres (Triton Technology, San Diego, Calif.). Left atrial injections of microspheres and reference blood sampling were performed at baseline, at the end of 90 minutes of ischema, and at 15 minutes and four hours of reperfusion.

Measurement of Myocardial Neutrophil Accumulation

Tissue samples of 0.4 grams were taken from the non-ischemic zone and from the non-necrotic and necrotic regions of the area at risk for spectrophotometric analysis of myeloperoxidase (MPO) activity ($\delta$ absorbance/minute), for assessment of neutrophil (PMN) accumulation in myocardium, as described previously in J. E. Jordan, et al., supra.

PMN Adherence to Post-experimental Coronary Artery Endothelium

PMN adherence to post-experimental coronary arteries was used as a bioassay of basal endothelial function. Canine PMNs were isolated from arterial blood and fluorescent labeled as previously described in Z.-Q. Zhao, et al., "Adenosine $A_2$-receptor activation inhibits neutrophil-mediated injury to coronary endothelium," *Am. J Physiol.*, 271:H1456, 1996. After excision of the heart, ischemic-reperfused LAD and non-ischemic LCx segments were isolated, cut into 3-mm segments, opened to expose the endothelium while being submerged in ice-cold K-H buffer, and then placed in dishes containing K-H buffer at 37° C. After unstimulated, fluorescent-labeled PMNs ($6 \times 10^6$ cells/dish) were incubated with postexperimental segments for 15 minutes, the coronary segments were washed of non-adherent PMNs, mounted on glass slides, and adherent PMNs were counted under epifluorescence microscopy (490-nm excitation, 504-nm emission), as described in V. H. Thourani, et al., "Ischemic preconditioning attenuates postischemic coronary artery endothelial dysfunction in a model of minimally invasive direct coronary artery bypass grafting," *J. Thorac. Cardiovasc. Surg.*, 117:383–389, 1999.

Agonist-stimulated Macrovascular Relaxation

Agonist-stimulated vasoreactivity in epicardial macrovessels from ischemic (LAD) and nonischemic (Lcx) was studied using the organ chamber technique. See, Z.-Q. Zhao, et al, supra. Indomethacin (10 $\mu$mol/L) was used to inhibit prostaglandin release. Coronary rings were precontracted with the thromboxane $A_2$ mimetic U-46619 (5 nmol/L). Endothelial function was assessed by comparing the vasorelaxation responses to incremental concentrations of acetylcholine (1–686 $\mu$mol/L) and A23187 (1–191 $\mu$mol/L), whereas smooth muscle function was assessed with sodium nitroprusside (1–381 $\mu$mol/L).

EXAMPLE 3

In vitro Studies

PMN Degranulation

Supernatant MPO activity was measured as the product of canine PMN degranulation using the method by Ely as modified by Jordan, et al., "$A_3$ adenosine receptor activation attenuates neutrophil function and neutrophil-mediated reperfusion injury," *Am. J. Physiol.* (In press). Canine PMNs ($20 \times 10^6$ cells/ml) were incubated in the presence or absence of ODS-HEP and stimulated to degranulate with platelet activating factor (PAF, 10 $\mu$M) and cytochalasin B (5 $\mu$g/ml). MPO activity in supernatants was assayed spectophotometrically.

PMN Adherence to Normal Coronary Artery Endothelium

Adherence of PMNs to normal canine epicardial arteries was assessed using coronary segments and PMNs from normal animals. Unstimulated PMNs and coronary artery segments prepared and labeled as described for adherence studies were coincubated in the presence or absence of heparin or O-desulfated heparin. After PAF (100 nM) stimulation, adherent PMNs were counted as outlined earlier.

Experiments with Human Umiblical Vein Endothelial Cells (HUVEC)

Primary HUVECs were isolated according to the method of Jaffe, et al., "Culture of human endothelial cells derived from umbilical veins: identification by morphological criteria," *J. Clin. Invest.* 52:2745–2750, 1973, cultured on coverslips using endothelial cell growth medium (Clonetics) and tested for expression of von Willebrand's factor. HUVECs were washed twice with PBS and incubated in Neuman/Tytell medium alone for 24 hours, followed by incubation with lipopolysaccharide (1 $\mu$g/ml) plus 10–20 ng/ml TNF$\alpha$ for 2 h, or in heparin or ODS-HEP (200 $\mu$g/ml) for 4 h with the addition of lipopolysaccharide and TNF$\alpha$ after 2 hours. HUVECs were fixed for 20 minutes on ice with 4% paraformaldehyde in CEB (10 mM Tris-HCl, pH 7.9, 60 mM KCl, 1 mM EDTA, 1 mM dithiothreitol) with protease inhibitors, PI (1 mM Pefabloc, 50 $\mu$g/ml antipain, 1 $\mu$g/ml leupeptin, 1 $\mu$g/ml pepstatin, 40 $\mu$g/ml bestatin, 3 $\mu$g/ml E-64, and 100 $\mu$g/ml chymostatin), permeabilized for 2 minutes with 0.1% NP40 in CEB/PI, washed once with cold CEB and fixed as before for 10 minutes. Coverslips were incubated in 3% $H_2O_2$ for 30 min to suppress peroxidase, washed three times in cold PBS, blocked for 2 h with 2% bovine serum albumin (BSA) in PBS on ice and incubated overnight at 4° C. with 1 $\mu$g/ml of anti-p65 antibody (Santa Cruz Biotechnology, Santa Cruz, Calif.) diluted in 0.1% BSA/PBS. Unbound anti-p65 was washed away with 2% BSA/PBS and bound antibody was incubated with biotinylated swine anti-rabbit immunoglobulin (1:1000) in 0.1% BSA/PBS for 45 minutes on ice, followed by 3 washes with 2% BSA/PBS. Coverslips were then incubated with streptavidin biotin peroxidase at room temperature for 1 hour, washed again, incubated in 0.03% wt/vol 3-3'diaminobenzidine with 0.003% $H_2O_2$ until a brown reaction product could be seen, counterstained with eosin and viewed under light microscopy.

Electrophoretic mobility shift assays (EMSAs) were also used to study the translocation of NF-$\kappa$B from the cytoplasm to the nucleus. Nuclear proteins were obtained from HUVEC as described by Digman, et al., "Accurate transcription initiation by RNA polymerase II in a soluble extract from isolated mammalian nuclei," *Nucleic Acid Res.*, 11:1475–1481, 1983, with the addition of the following proteinase inhibitors: 1 mM phenylmethylsulfonyl fluoride, 1 $\mu$g/ml pepstatin A, 0.5 $\mu$g/ml chymostain, 1 $\mu$g/ml antipain, 1 $\mu$g/ml leupeptin and 4 $\mu$g/ml aprotinin. The double stranded oligonucleotide DNA probe of the NF-$\kappa$B consensus sequence AGTTGAGGGGACTTTCCCAGGC was 5'OH end-labeled with [$\gamma^{32}$P]ATP using polynucleotide kinase (Santa Cruz). Free radionucleotide was removed using a Sephadex G-25 column. The probe (0.5 ng) was incubated with 10 $\mu$g HUVEC nuclear protein (Bio-Rad method) in 20 $\mu$l buffer containing a final concentration of 10 Mm HEPES, Ph 7.5, 50 mM KCl, 5 mM $MgCl_2$, 1 mM dithiothreitol, 1 mM EDTA and 5% glycerol, plus 5 $\mu$g of poly (dI-dC) to reduce nonspecific binding. Incubations were carried out at room temperature for 20 minutes. Reactions were electrophoresed at 14 V/cm for 1.5–2.0 hours on a 6% nondenaturing polyacrylamide gel in 0.5×TBE (45 mM Tris borate, 25 mM boric acid, 1 mM EDTA) at 4° C., and autoradiographed at −80° C.

Experiments with Isolated Perfused Rat Hearts

Male Sprague-Dawley rats (300–400 g) were anesthetized with sodium pentobarbital (40 mg/kg, i.p.), and the hearts were quickly excised and perfused in a Langendorff apparatus as described by J. A. Watt, et al., "Trace amounts of albumin protect against ischemia and reperfusion injury in isolated rat hearts," *J. Mol. Cell. Cardiol.*, 31:1653–1662, 1999 with modified Krebs-Henseleit bicarbonate buffer (KHB), consisting of 118 mM NaCl, 4.7 mM KCl, 1.2 mM $KH_2PO_4$, 1.2 mM $MgSO_4$7 $H_2O$, 3.0 mM $CaCl_2 2H_2O$ (yielding 2.5 mM free $Ca^{2+}$ in the presence of EDTA), 0.5 mM EDTA, 11 mM dextrose, and 25 mM $NaCHO_3$. Three groups were studied: 1) nonischemic control hearts were perfused 45 minutes; 2) ischemic-reperfused hearts were subjected to 15 minutes warm global ischemia and 15 minutes reperfusion; and 3) ODS-HEP hearts from rats injected with 6 mg/mg ODS-HEP i.v. 120 minutes before heart excision were subjected to 15 minutes each of global ischemia and reperfusion, with 100 μg/ml ODS-HEP in perfusion buffer. After perfusion, ventricles were frozen with Wollenberger clamps precooled in liquid $N_2$, and pulverized under liquid $N_2$. Nuclear proteins were immediately isolated from frozen myocardial powders of by the method of Li, et al., "Early activation of transcription factor NF-κB during ischemia in perfused rat heart," *Am. J. Physiol.*, 276 (*Heart Care Circ. Physiol.* 45);H543–H552, 1999. EMSAs were performed using 15 μg of nuclear protein in each binding reaction. Competition experiments were performed by incubation of nuclear proteins with 10× unlabeled NF-κB or cyclic-AMP responsive element oligonucleotides (CRE, AGAGATTGCCTGACGTCAGAGAGCTAG) for 5 minutes prior to addition of $^{32}$P-labeled NF-κB probe. Supershift assays were performed by adding 0.5 μg of antibodies to p65 and p50 components of NF-κB (Santa Cruz) to the binding reaction after labeled probe. Reactions were electrophoresed at 100 V for 2 hour at room temperature on a 5% nondenaturing polyacrylamide gel in 0.5×TGE (120 mM glycine, 1 mM EDTA, 25 mM Tris, pH 8.5) and autoradiographed.

Statistical Analysis

The data were analyzed by one-way analysis of variance or repeated measures two-way analysis of variance for analysis of group, time and group-time interactions. If significant interactions were found, Tukey's or Student-Newman-Keuls post hoc multiple comparisons tests were applied to locate the sources of differences. Differences in the densities of the p-65 containing NF-κB gel band between treated and untreated ischemic reperfused rat hearts were compared using the t test. A $p<0.05$ was considered significant, and mean±standard error of the mean (SEM) are reported.

EXAMPLE 4

Using the procedures described above, heparin and O-desulfated anticoagulant heparin were found to significantly reduce myocardial infarct size. As shown in FIGS. 1A and 1B, the area at risk (AAR) is expressed as a percentage of the left ventricle (LV). The infarct size (area of necrosis, AN) is expressed as a percentage of the area at risk (AAR). Columns represent group means±SEM. *$p<0.05$ versus Control. HEP or ODS-HEP treatment decreased infarct size (area of necrosis, AN), expressed as a percentage of the area at risk (AN/AAR), by 35% and 38%, respectively, compared to Controls. There was no statistical difference in size of infarcts between the HEP and ODS-HEP groups, and the area at risk from LAD occlusion, expressed as a percentage of the left ventricular mass (AAR/LV), was comparable among groups.

As shown in FIG. 2, plasma creatine kinase (CK) activity was used to confirm histologic measurement of infarct size during the time course of the experiment. Values are means±SEM. *$p<0.05$ HEP and ODS-HEP versus Control and * $p<0.05$ versus the previous time point in the same group. There were no significant differences in plasma CK activity at baseline among groups and no increases in CK activity after regional ischemia. Hearts in the Control group showed a steep rise in CK activity within the initial hour of reperfusion, which was significantly reduced by HEP or ODS-HEP treatment, consistent with the smaller infarct sizes in these groups.

Figure 3:
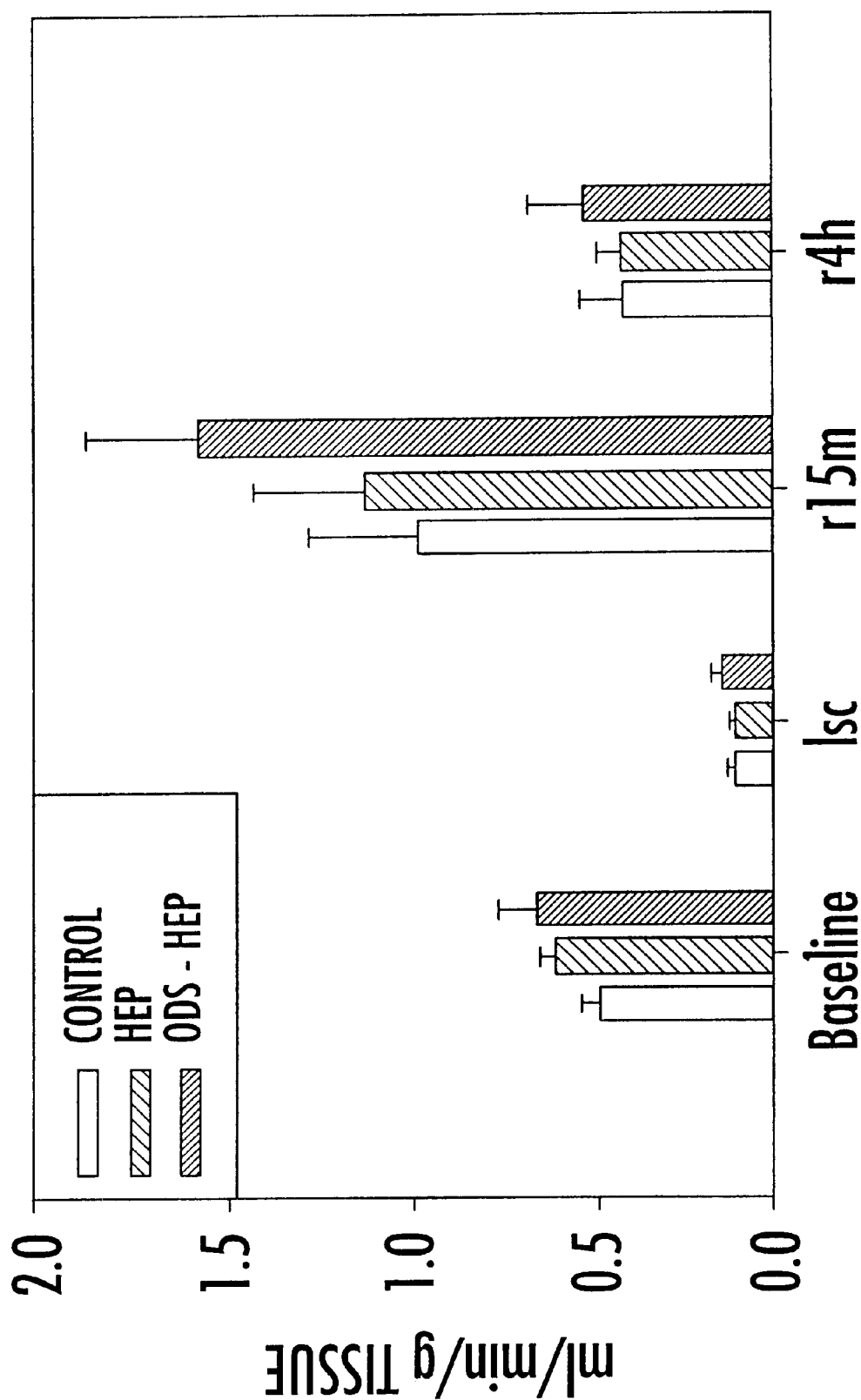
FIG. 3 shows that heparin and O-desulfated nonanticoagulant heparin do not alter regional myocardial collateral blood flow.

Despite their favorable effects on infarct size, HEP and ODS-HEP produced no significant changes in myocardial blood flow. Subendocardial blood flow in the ischemic-reperfused LAD coronary artery region was statistically comparable among the three groups at baseline as shown by the graphs in FIG. 3. Regional myocardial blood flow is shown in the area at risk (AAR) which is in the distribution of the ischemic-reperfused left anterior descending (LAD) coronary artery. There were also no differences in regional myocardial blood flow in the distribution of the non-ischemic-reperfused left circumflex (LCx) coronary artery. Transmural blood flow in the area at risk was significantly decreased during ischemia, with no group differences. All groups showed a comparable hyperemic response in the area at risk at 15 minutes of reperfusion, after which blood flow was diminished to similar levels in all groups by four hours. In the non-ischemic-reperfused LCx coronary artery region, transmural blood flow was comparable in all groups throughout the protocol (data not shown).

Differences in infarct size were also not from hemodynamic or cardiodynamic differences. Hemodynamics at baseline and during ischemia and reperfusion were comparable among groups (data not shown). Heart rate was significantly increased during ischemia and reperfusion in all animals, and left ventricular end diastolic pressure was comparably elevated during ischemia in all three groups. Following ischemia, hearts in all groups demonstrated dyskinesis in the area at risk. All hearts showed poor recovery of percent systolic shortening throughout the four hours of reperfusion, and diastolic stiffness (as measured by the valueless β-coefficient) increased following ischemia to comparable levels in all groups as shown in Table I below.

TABLE I

REGIONAL SYSTOLIC AND DIASTOLIC CARDIODYNAMIC VARIABLES

|  | Baseline | Ischemia | r15min | r1hr | r2hr | r3hr |
| --- | --- | --- | --- | --- | --- | --- |
| % SS |  |  |  |  |  |  |
| Control | 26 ± 2 | −7 ± 2* | −4 ± 2 | −4 ± 2 | −5 ± 1 | −5 ± 1 |
| HEP | 26 ± 3 | −4 ± 1* | −0.4 ± 2 | −2 ± 2 | −4 ± 2 | −6 ± 3 |
| ODS-HEP | 24 ± 4 | −5 ± 1* | −2 ± 3 | −2 ± 3 | −9 ± 3 | −6 ± 4 |

TABLE I-continued

REGIONAL SYSTOLIC AND DIASTOLIC CARDIODYNAMIC VARIABLES

|  | Baseline | Ischemia | r15min | r1hr | r2hr | r3hr |
|---|---|---|---|---|---|---|
| Diastolic Stiffness (unitless β Coefficient) | | | | | | |
| Control | 0.2 ± 0.05 | 0.5 ± 0.2 | 1.0 ± 0.4 | 1.0 ± 0.3 | 1.0 ± 0.3 | 0.6 ± 0.2 |
| HEP | 0.2 ± 0.04 | 0.6 ± 0.1* | 0.8 ± 0.2 | 1.0 ± 0.2 | 1.0 ± 0.2 | 1.0 ± 0.2 |
| ODS-HEP | 0.2 ± 0.04 | 0.8 ± 0.2* | 1.0 ± 0.6 | 1.0 ± 0.2 | 0.9 ± 0.5 | 0.7 ± 0.2 |

% SS = percent systolic shortening.
Baseline = prior to left anterior descending (LAD) coronary artery occlusion;
Ischemia = at the end of 90 minutes of LAD ischemia;
r15min, r1hr, r2hr, r3hr, and r4hr = minutes or hours of reperfusion following ischemia.
Values are mean ± standard error of the mean.
*p < 0.05 versus previous time point within the same treatment group.

EXAMPLE 5

Using the procedures described above, heparin and O-desulfated heparin were found to reduce PMN accumulation in reperfused myocardium. PMN influx is a major mechanism underlying lethal reperfusion injury. Treatment with HEP or ODS-HEP significantly reduced MPO activity in necrotic myocardium by 50% compared to the Control group as shown in FIG. 4. In FIG. 4 myeloperoxidase activity, an index of PMN accumulation, is shown in normal, ischemic, and necrotic myocardial tissue samples from each group. *p<0.05 HEP and ODS-HEP versus Control. PMN accumulation within normal myocardium was low and comparable among Control, HEP and ODS-HEP groups (16±8, 18±11, and 18±8 δ absorbance units/minute, respectively). HEP and ODS-HEP both decreased MPO activity in the nonnecrotic area at risk, but these changes did not achieve significance (p>0.10).

EXAMPLE 6

Despite reducing infarct size, ODS-HEP did not produce anticoagulation. As shown in FIG. 5, systemic whole blood anticoagulation was studied using the activated clotting time, measured in seconds. *p<0.05 HEP versus other groups. At four hours of reperfusion, activated clotting time (ACT) was increased greater than ten-fold after HEP treatment compared with Control (1425±38 seconds versus 123±10 seconds, respectively). In contrast, ACT in the ODS-HEP group (145±10 seconds) was not different from Controls (123±10 seconds, p=0.768). Thus, ODS-HEP was able to effect the same benefits as HEP without anticoagulation.

EXAMPLE 7

This example shows that heparin and O-desulfated heparin reduce neutrophil adherence and endothelial dysfunction in coronary arteries. ODS-HEP did not significantly reduce PAF-stimulated PMN degranulation (data not shown), suggesting that ODS-HEP has little direct effect on PMN activity. However, PAF-stimulated PMN attachment to coronary endothelium was significantly reduced by both HEP and ODS-HEP in a dose-dependent manner (FIG. 6). Neutrophil adherence to normal coronary endothelium was stimulated by 100 nM platelet activating factor (PAF) added to medium and was inhibited in a dose-dependent manner by heparin or ODS-HEP. *p<0.05 HEP group versus HEP control, @p<0.05 HEP group versus 0 mg HEP group, *p<0.05 ODS-HEP versus ODS control and #p<0.05 ODS-HEP versus 0 mg ODS group.

Inhibition of PMN adherence to PAF-stimulated coronary endothelium was charge dependent, as suggested by reversal of the inhibiting effects of the polyanions HEP or ODS-HEP on attachment by the polycation protamine (PMNs/mm$^2$ endothelium=66±3 with 100 µg/ml HEP vs 180±8 with HEP+1 mg/ml protamine; 86±4 with 100 µg/ml ODS-HEP vs 136±4 with ODS-HEP+1 mg/ml protamine; *p<0.05 for both).

HEP and ODS-HEP also reduced PMN adherence to ischemic-reperfused coronary endothelium in vivo. The bar graph in FIG. 7 shows that PMN adherence to the ischemic-reperfused LAD coronary artery was increased by 300% in the untreated Control group compared to the non-ischemic-reperfused LCx artery. Neutrophil (PMN) adherence to coronary endothelium was quantitated as the number of adherent PMNs/mm$^2$ of coronary endothelium. LCx=the non-ischemic-reperfused left circumflex coronary artery, LAD=the ischemic-reperfused left anterior descending coronary artery. *p<0.05 HEP and ODS-HEP versus LAD control. HEP or ODS-HEP reduced PMN adherence to the ischemic-reperfused LAD by 51 and 42%, respectively, compared to untreated Controls (FIG. 7).

HEP and ODS-HEP also preserved receptor-mediated vasodilator responses of coronary endothelium following ischemia and reperfusion. To quantify agonist-stimulated endothelial dysfunction in epicardial coronary arteries, we studied the vascular response to incremental concentrations of the vasodilators acetylcholine (endothelial-dependent; receptor-dependent), A23187 (endothelial-dependent; receptor-independent), and sodium nitroprusside (direct smooth muscle) in post-ischemic coronary vascular ring preparations.

FIG. 8 illustrates vasodilator responses to acetylcholine in isolated coronary rings from the ischemic-reperfused LAD, expressed as a percentage of U46619-induced precontraction. In the Control group, there is a statistically significant shift to the right in the concentration-response curve, representing reduced relaxation to acetylcholine. In contrast, the relaxant effect of coronary vessels to acetylcholine was preserved by HEP or ODS-HEP treatment. Response curves are shown to incremental concentrations of acetylcholine (Ach) in the ischemic-reperfused left anterior descending (LAD) coronary artery precontracted with U46619. *p<0.05 HEP and ODS-HEP versus Control and *p<0.05 HEP versus Control.

The concentration of acetylcholine required to effect 50% relaxation (EC$_{50}$; −log [M]) was significantly greater for the Control (−6.975±0.06) compared to the HEP (−7.298±0.06) or ODS-HEP (−7.201±0.05) groups (p<0.05). There were no differences in non-ischemic-reperfused ring preparations from LCx (data not shown). In addition, there were no differences between LAD versus LCx vasodilator responses to A23187 (maximal relaxation=122±4 and 120±7% and $EC_{50}$ log [M]=−7.18±0.06 and −7.17±0.09 for LAD and LCx, respectively) or sodium nitroprusside (maximal relaxation=129±5 and 121±4% and $EC_{50}$ log [M]=−7.31±0.02 and −7.29±0.04 for LAD and LCx, respectively), and responses were unaffected by HEP or ODS-HEP.

EXAMPLE 8

This example shows that O-desulfated nonanticoagulant heparin prevents activation of nuclear factor-κB. Based on the possibility that a polyanion such as heparin might bind to and charge neutralize the NLF, immunohistochemical staining for NF-κB in unstimulated control cells was studied to determine whether heparin could inhibit translocation of NF-κB to the nucleus. FIG. 9A shows brown staining for antibody to the p65 NF-κB component present in the cytoplasm of HUVEC, but not in nuclei. In TNF stimulated HUVECs, some, but not all nuclei, stain positive for anti-p65 (FIG. 9B), corresponding to nuclear translocation of NF-κB. ODS-HEP (FIG. 9C) or HEP (data not shown) treatment prevents TNF-stimulated anti-p65 nuclear staining.

Interruption of endothelial NF-κB activation by heparin and O-desulfated nonanticoagulant heparin was confirmed by electrophoretic mobility shift assays (EMSAs) as shown in FIG. 10. TNF stimulates endothelial DNA binding of NF-κB (FIG. 10, lane 2) compared to untreated controls (lane 1). Pretreatment with 200 μg/ml ODS-HEP eliminates NF-κB binding activity (lane 3), confirming that heparin prevents translocation of NF-κB to the nucleus. HUVECs were stimulated with 10 ng/ml TNFα for one hour and nuclear protein was harvested for electrophoretic mobility shift assays to detect binding of NF-κB, using the oligonucleotide consensus AGTTGAGGGGACTTTCCCAGGC, end-labeled with [$\gamma^{32}P$]ATP. Treatment of monolayers with TNF stimulates DNA binding of NF-κB (lane 2) compared to untreated controls (lane 1). Pretreatment of cells with 200 μg/ml ODS-HEP virtually eliminates NF-κB binding activity in nuclear protein extracts (lane 3), confirming that heparin prevents translocation of NF-κB from the cytoplasm to the nucleus.

O-desulfated nonanticoagulant heparin also reduced DNA binding of NF-κB in ischemic-reperfused myocardium. Exposure of rat hearts to 15 minutes warm global ischemia and 15 minutes reperfusion increased DNA binding of myocardial nuclear protein to oligonucleotide sequences for NF-κB (FIG. 11A, lane 2).

Figure 11A:
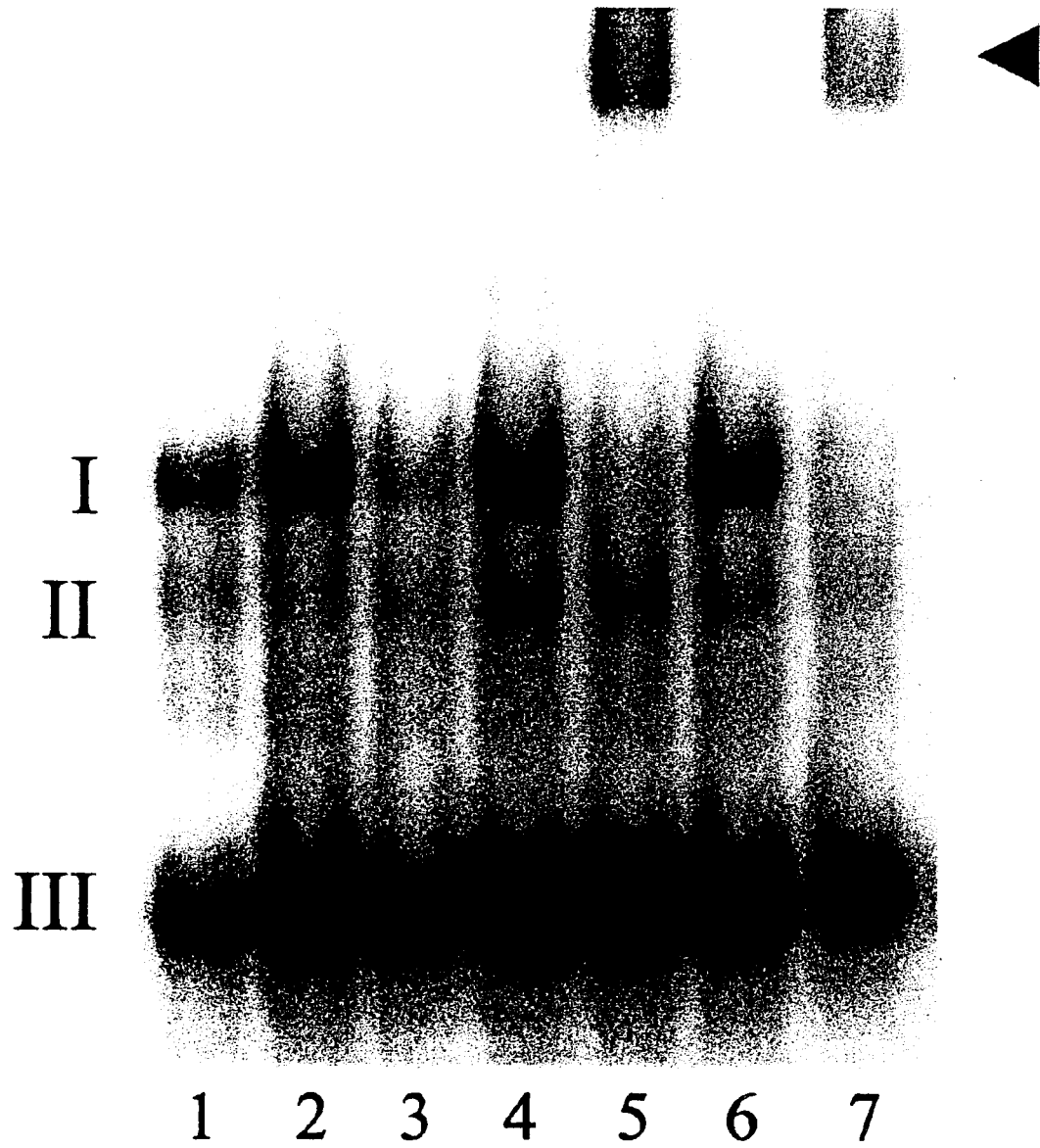
FIG. 11B illustrates competition experiments performed by incubation of nuclear proteins with unlabeled NF-κB or cyclic-AMP responsive element oligonucleotides.
Figure 11B:
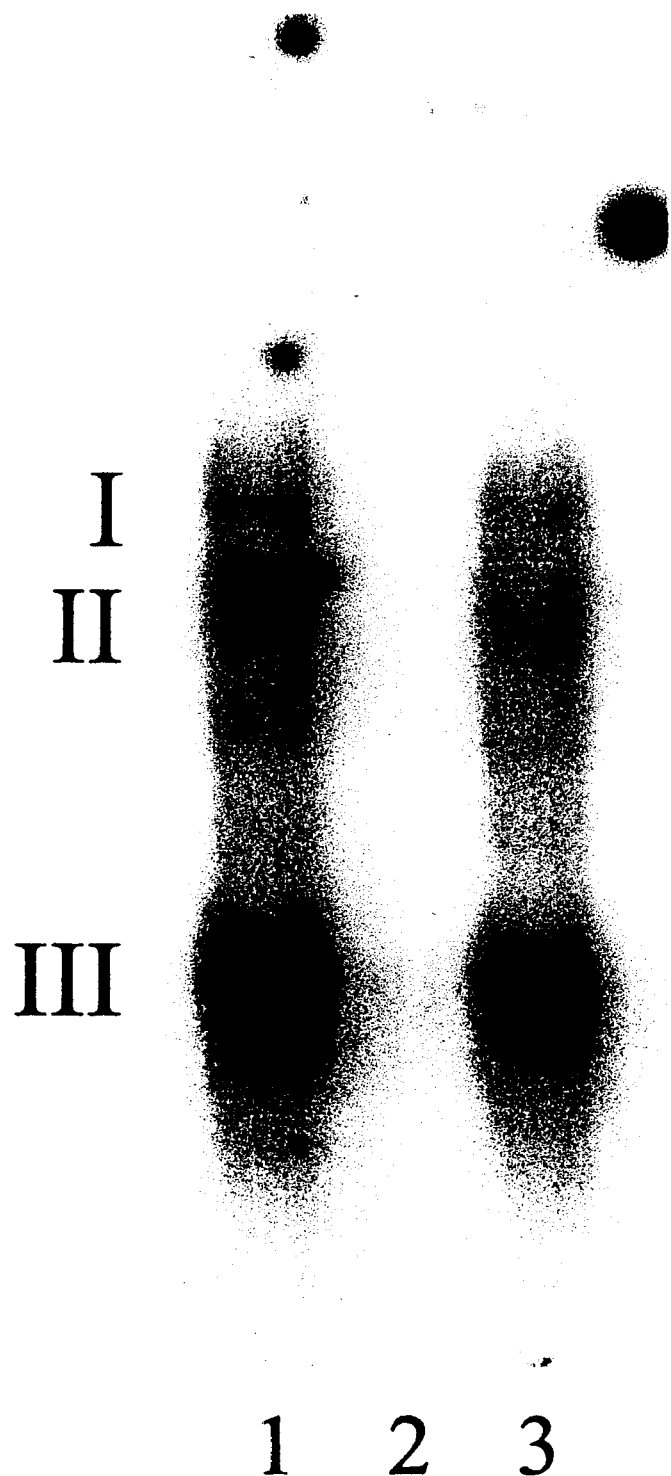

Three distinct bands of increased DNA binding were observed, all of which were eliminated by addition of excess unlabeled NF-κB oligonucleotide probe (FIG. 11B, lane 2). FIG. 11B illustrates competition experiments performed by incubation of nuclear proteins with 10× unlabeled NF-κB (lane 2) or cyclic-AMP responsive element oligonucleotides (CRE, AGAGATTGCCTGACGTCAGAGAGCTAG, lane 3) for 5 minutes prior to addition of $^{32}P$-labeled NF-κB probe. Compared to binding reactions without excess unlabeled probe (lane 1), addition of unlabeled NF-κB blocked DNA binding in all three complexes.

Supershift experiments identified complex I as the band containing the p65 component of NF-κB (FIG. 11A, lane 5). ODS-HEP treatment reduced ischemia-reperfusion related stimulation of NF-κB binding to DNA in all three bands (FIG. 11A, lane 3). DNA binding of the p65-containing complex I was nearly eliminated by ODS-HEP, with a reduction of 54±6% as measured by densitometry in comparison to complex I of untreated ischemic-reperfused rat hearts (p<0.05, n=4). Thus, in addition to directly attenuating vascular adherence of PMNs to coronary endothelium, decreasing PMN accumulation in the area at risk and reducing myocardial necrosis, HEP or ODS-HEP also interrupt NF-κB activation and possibly adhesion molecule expression.

Langendorf perfused rat hearts were subjected to 15 minutes warm global ischemia followed by 15 minutes reperfusion. Nuclear protein was then harvested for EMSAs to measure DNA binding of NF-κB. Compared to sham perfused control hearts (lane 1), ischemia and reperfusion typically increased DNA binding of myocardial nuclear protein to oligonucleotide sequences for NF-κB (lanes 2 and 4). Three distinct complexes were identified. Supershift experiments performed with antibody to p65 (lane 5), are antibody to p65 and p50 (lane 7) demonstrated complex I to be shifted (arrow), identifying it as the band containing the p65 component of NF-κB. Pretreatment and perfusion with ODS-HEP (6 mg/kg iv 2 hours prior to heart perfusion; 100 μg/ml in perfusate) prevented the ischemia-reperfusion related stimulation of NF-κB DNA binding of the p65-containing complex I (lane 3). DNA binding of the p65-containing complex I was nearly eliminated by ODS-HEP, with a reduction of 54±6% as measured by densitometry in comparison to complex I of untreated ischemic-reperfused rat hearts (p<0.05, n=4).

EXAMPLE 9

This example shows that ODS-heparin reduces contractile dysfunction following ischemia and reperfusion of isolated rat hearts. After 15 minutes of both ischemia and reperfusion, hearts recovered high contractile function (95% of baseline, ischemia-reperfusion; and 93% of baseline, ODS-HEP ischemia-reperfusion). Therefore, in additional studies, the period of ischemia was increased 30 minutes. Both untreated and ODS-HEP treated hearts had reduced contractile function after 30 minutes of ischemia and 15 minutes of reperfusion (Pressure Rate Product=36,780±2, 589 for Sham vs 4,575±1,856 for Ischemic-Reperfused and 10,965±2,908 mm Hg/min for ODS-HEP treated Ischemic-Reperfused hearts, n=4 each), but hearts treated with ODS-HEP had significantly improved recovery of contractile function, which was 2.4 times better than that observed in hearts that did not receive ODS-HEP (p<0.05). Thus, in this severe model, ODS-HEP reduces both molecular and physiologic consequences of ischemia and reperfusion.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for inhibiting apoptosis in ischemic-reperfused myocardium comprising administering to a human in need thereof from 3 mg/kg to 100 mg/kg of heparin to reduce apoptisis cell death in myocardial infarction.

2. The method according to claim 1 wherein said administering inhibits apoptosis in ischemic-reperfused brain, reducing neuronal cell death in stroke.

3. The method according to claim 1 wherein said administering inhibits apoptosis in the failing heart, reducing apoptosis cell death in congestive heart failure and cardiomyopathy.

4. A method for inhibiting apoptosis in ischemic-reperfused cyocardium comprising administering to a human in need thereof an effective amount of nonanticoagulant heparin to reduce apoptosis cell death in myocardial infarction.

5. The method according to claim 4 wherein said nonanticoagulant heparin is an O-desulfated heparin.

6. The method according to claim 4 wherein said nonanticoagulant heparin is a N-desulfated heparin.

7. The method according to claim 4 wherein said effective amount of heparin is from 3 mg/kg to 100 mg/kg.

8. The method according to claim 4 wherein said administering inhibits apoptosis in ischemic-reperfused brain, reducing neuronal cell death in stroke.

9. The method according to claim 8 wherein said nonanticoagulant heparin is an O-desulfated heparin.

10. The method according to claim 8 wherein said nonanticoagulant heparin is a N-desulfated heparin.

11. The method according to claim 4 wherein said administering inhibits apoptosis in the failing heart, reducing apoptosis cell death in congestive heart failure and cardiomyopathy.

12. The method according to claim 11 wherein said anticoagulant heparin is an O-desulfated heparin.

13. The method according to claim 11 wherein said anticoagulant heparin is a N-desulfated heparin.

14. A method for enhancing the anti-apoptotic effect of heparin or nonanticoagulant heparin comprising conjugating heparin or nonanticoagulant heparin to a lipophilic moiety by reaction across a carboxylic acid or free amine group to enhance cellular uptake by cell types not normally concentrating heparin.

* * * * *

UNITED STATES PATENT AND TRADEMARK OFFICE
CERTIFICATE OF CORRECTION

PATENT NO.    : 6,489,311 B1
DATED         : December 3, 2002
INVENTOR(S)   : Kennedy It is certified that error appears in the above-identified patent and that said Letters Patent is hereby corrected as shown below:

Title page,
Item [56], References Cited, OTHER PUBLICATIONS,
"H. Akimoto et al.," reference reads "Molicules" should read -- Molecules --;
"H. Zou et al.," reference reads "Dependents" should read -- Dependent --.
"F.G. Wulczyn, et al.," reference reads "kb" should read -- kB --;
"A.A. Beg, et al.," reference reads "NF13 kB" should read -- NF-kB --.

Column 19,
Line 6, "cyocardium" should read -- myocardium --.

Column 20,
Line 3, "claim 4" should read -- claim 3 --.

Signed and Sealed this

Twenty-ninth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,489,311 B1
DATED        : December 3, 2002
INVENTOR(S)  : Kennedy It is certified that error appears in the above-identified patent and that said Letters Patent is hereby corrected as shown below:

Column 18,
Line 63, "apoptisis" should read -- apoptosis --.

Signed and Sealed this

Fourteenth Day of December, 2004

JON W. DUDAS
*Director of the United States Patent and Trademark Office*